United States Patent
De Block

(10) Patent No.: US 7,951,990 B2
(45) Date of Patent: May 31, 2011

(54) METHOD AND MEANS FOR DETERMINING FITNESS IN PLANTS

(75) Inventor: Marc De Block, Merelbeke (BE)

(73) Assignee: Bayer Bioscience N.V., Ghent (BE)

( * ) Notice: Subject to any disclaimer, the term of this patent is extended or adjusted under 35 U.S.C. 154(b) by 25 days.

(21) Appl. No.: 11/451,325

(22) Filed: Jun. 13, 2006

(65) Prior Publication Data

US 2006/0230469 A1 Oct. 12, 2006

Related U.S. Application Data

(62) Division of application No. 10/468,218, filed as application No. PCT/EP02/01991 on Feb. 19, 2002, now Pat. No. 7,084,320.

(30) Foreign Application Priority Data

Feb. 19, 2001 (EP) ..................................... 01200576

(51) Int. Cl.
*A01H 4/00* (2006.01)

(52) U.S. Cl. ......... 800/268; 800/260; 800/298; 435/468

(58) Field of Classification Search .................. 800/268, 800/260; 435/410
See application file for complete search history.

(56) References Cited

U.S. PATENT DOCUMENTS 5,746,023 A 5/1998 Hanafey et al.
6,074,876 A * 6/2000 De Block ...................... 435/468

FOREIGN PATENT DOCUMENTS

WO WO-99/52345 A 10/1999

OTHER PUBLICATIONS

Gibson et al. 2000. Physiologia Plantarum 110: 469-476.*
Goffman et al. 2001. Crop Science 41: 1072-1079.*
Ishikawa Masaya et al., Plant Science (Limerick), vol. 107, No. 1, 1995, pp. 83-93.
Lichtenthaler Hartmut K. et al., Plant Physiology and Biochemistry (Paris) vol. 38, No. 11, Nov. 2000, pp. 889-895.
Xie et al., Plant Physiol., No. 120, pp. 217-225 (1999).

* cited by examiner

*Primary Examiner* — Medina A Ibrahim
*Assistant Examiner* — Keith O. Robinson
(74) *Attorney, Agent, or Firm* — Birch, Stewart, Kolasch & Birch, LLP

(57) ABSTRACT

The present invention provides methods and means for determining parent inbred plant lines with good combining ability, for determining good combinations of parent inbred plant lines capable of yielding hybrid lines with high heterosis, and further for determining the agronomical performance of different plant lines, which can be performed in vitro by determining the electron flow in the mitochondria under control and stress conditions.

10 Claims, 14 Drawing Sheets

METHOD AND MEANS FOR DETERMINING FITNESS IN PLANTS

CROSS REFERENCE TO RELATED APPLICATIONS

This application is a divisional application of application Ser. No. 10/468,218 filed on Aug. 18, 2003, now U.S. Pat. No. 7,084,320 which is the national phase of PCT International Application No. PCT/EP02/01991 filed Feb. 19, 2002, which claims priority on European Application No. 01200576.5 filed on Feb. 19, 2001. The entire contents of the above-identified applications are hereby incorporated by reference.

The present invention provides methods and means for determining parent inbred plant lines with good combining ability, for determining good combinations of parent inbred plant lines capable of yielding hybrid lines with high heterosis, and further for determining the agronomical performance of different plant lines, which can be performed in vitro.

BACKGROUND

A plant line can be called vigorous when this line grows vitally, healthy, is tolerant to various biotic and abiotic stresses and most importantly has a high yield.

The currently used method to classify plant lines according to their growth and yield vigour consists in performing field trials at different locations. A disadvantage of field trials is that, at best, only two experiments can be done each year. Even when field trials are planned very well and deliver the appropriate data, this time constraint interferes with the continuity of the projects and slows down the progress.

A number of assays (mainly qualitative) have been described for use in plant tissue culture to study the effect of various stresses on the survival of cells or tissues (Towill and Mazur, 1975; Chen et al. 1982, Duncan and Widholm 1990, Stepan-Sarkissian and Grey, 1990; Upadhyaya and Caldwell, 1993; Enikeev et al., 1995; Ishikawa et al., 1995; Popov and Vysotskaya, 1996). These are actually "viability" assays which do not measure the fitness or vigour of the cultures.

Chlorophyll fluorescence and fluorescence imaging may also be used to study the influences of stress conditions on whole plants (Lichtenthaler, 1996; Lichtentaler and Mieké, 1997). Although these assays provide some data on the tolerance of the plant lines to certain stresses, they cannot be used to measure growth and yield vigour.

Published PCT application "WO" 97/06267 and U.S. Pat. No. 6,074,876 (incorporated herein by reference) describe the use of PARP inhibitors to improve the transformation (qualitatively or quantitatively) of eukaryotic cells, particularly plant cells. Also described is a method for assessing the agronomical fitness of plants or plant material by measuring the electron flow in the mitochondrial electron transport chain.

None of the prior art documents describe an in vitro method allowing to predict the combining ability of parent inbred plant lines, nor do they describe an in vitro method allowing to determine good combinations of parent inbred plant lines capable of yielding hybrid lines with high heterosis. Such in vitro physiological methods would represent an extra tool to rapidly identify parental and hybrid lines of interest in breeding programs and could result in a significant gain of time.

The current invention provides such methods as described in the various embodiments and claims disclosed herein.

SUMMARY OF THE INVENTION

The invention provides a method for selecting a parent inbred plant line from a collection of parent lines, preferably a plant from the Brassicaceae, which upon crossing with another parent inbred plant line is capable of yielding a hybrid plant line with high heterosis effect comprising the steps of:
  a) culturing a population of explants, preferably selected from callus, hypocotyl explants, shoots, leaf disks and whole leaves, particularly a hypocotyl, of each of said parent inbred plant line of said collection under conditions which activate the metabolism in said explant, preferably by culturing on callus inducing medium for 1 to 10 days, particularly for about 5 days;
  b) measuring the electron flow in the mitochondrial electron transport chain in the population of explants, relative to the electron flow in the mitochondrial electron transport chain in a population of explants from a reference plant line of the same species, preferably of the same variety, preferably by measuring the capacity of said explant to reduce 2,3,5-triphenyltetrazolium chloride (TTC) or 3-(4,5-dimethylthiazol-2-yl)-2,3 diphenyl-2H-tetrazolium;
  c) selecting a parent inbred line which has a high, preferably the highest relative amount of electron flow in the mitochondrial electron transport chain.

The method may further comprise between step a) and step b) the step of incubating the explants for about 18 hours in a buffer comprising about 25 mM K-phosphate and about 2 to 3% sucrose.

It is another object of the invention to provide a method for determining in vitro the agronomical fitness of a plant line comprising the steps of:
  a) culturing a population of explants of the plant line under conditions which activate the metabolism in said explants;
  b) incubating, preferably for about 18 hrs, a first part of the population of cultured explants in a buffer solution, preferably a buffer solution comprises about 25 mM K-phosphate and about 2 to 3% sucrose;
  c) incubating, preferably for about 18 hours, a second part of the population of cultured explants in said buffer solution further comprising a salicylic acid derivative capable of generating oxidative stress in plant cells incubated in a solution of said salicylic acid derivative, preferably acetylsalicylic acid, particularly in a concentration of about 25 mg/L;
  d) measuring the electron flow in the mitochondrial electron transport chain in said first and second part of the population;
wherein the agronomically fit plants have a greater amount of electron flow in the first part of the cultured explants than in the second part of cultured explants.

It is yet another object of the invention to provide a method for selecting a plant line having the highest growth and yield vigour from a collection of plant lines from the same species (variety) comprising the steps of
  a) culturing a population of explants of each of the plant lines of said collection under conditions which activate the metabolism in said explants;
  b) incubating, preferably for about 18 hrs, a first part of the population of cultured explants in a buffer solution, preferably a buffer solution comprises about 25 mM K-phosphate and about 2 to 3% sucrose;
  c) incubating, preferably for about 18 hours, a second part of the population of cultured explants in the buffer solution further comprising a salicylic acid derivative capable of generating oxidative stress in plant cells incubated in a solution of the salicylic acid derivative, preferably acetylsalicylic acid, particularly in a concentration of about 25 mg/L;

d) measuring the electron flow in the mitochondrial electron transport chain in each of the first and second parts of the populations; and
e) selecting a plant which has a high amount of electron flow in the mitochondrial electron transport chain.

The invention also provides a method for producing a hybrid plant line, comprising the steps of:
a) assaying a collection of inbred lines of interest by
   i) culturing a population of explants (preferably a hypocotyl) of each of the inbred plant lines of the collection under conditions which activate the metabolism in the explant;
   ii) measuring the electron flow in the mitochondrial electron transport chain in the population of explants, relative to the electron flow in the mitochondrial electron transport chain in population of explants from a reference plant line of the same species, preferably of the same variety;
b) selecting a parent inbred line which has a high relative amount of electron flow in the mitochondrial electron transport chain when compared to other inbred lines from said collection;
c) crossing said selected inbred line with another inbred line;
d) collecting seed from said crossed selected inbred line.

Yet another object of the invention is to provide a method for producing a hybrid plant line, comprising the steps of:
a) assaying a collection of inbred lines of interest by
   i) culturing a population of explants (preferably a hypocotyl) of each of the parent inbred plant lines of the collection under conditions which activate the metabolism in the explants;
   ii) measuring the electron flow in the mitochondrial electron transport chain in the populations of explants, relative to the electron flow in the mitochondrial electron transport chain in a population of explants from a reference plant line of the same species, preferably of the same variety;
b) assaying the collection of inbred lines of interest by
   i) culturing a population of explants of each of the parent inbred plant lines of the collection under conditions which activate the metabolism in the explants;
   ii) incubating a first part of the each of the populations of the cultured explants in a buffer solution;
   iii) incubating a second part of each of the populations of the cultured explants in the buffer solution, further comprising a salicylic acid derivative capable of generating oxidative stress in plant cells incubated in a solution of said salicylic acid derivative, preferably acetylsalicylic acid, particularly in a concentration of about 25 mg/L;
   iv) measuring the electron flow in the mitochondrial electron transport chain in each of the first and second parts of said populations;
c) selecting at least one parent inbred line, preferably both parent inbred lines, which has a high relative amount of electron flow in the mitochondrial electron transport chain when compared to other inbred lines from said collection and which has a large negative difference between the measured electron flow in the mitochondrial electron transport chain between the second and the first part of the populations of explants;
d) crossing the selected inbred line with a second (inbred) line;
e) collecting seed from the crossed selected inbred line.

The experiments were done with two lines of *Brassica napus*. The line indicated as "control" has a seed yield comparable to the original N90-740. The less vigorous line has a about 10% lower seed yield as scored in field trials. The metabolism of the hypocotyl explants was activated by culturing the explants for several days on culture medium containing sucrose and hormones (A). The culture temperature has to be high enough to activate the metabolism (B). Although the incubation step with phosphate buffer pH7.4 containing 2% sucrose is not obligate, it improves the quality of the assay (C). The optimal phosphate concentration of the incubation medium is around 25 mM (D). Each value is the mean of three replicates with 150 explants per replicate. The error bars represent the standard error of the mean. In (A) (B) and (C) control line is represented by black bars, whereas the less vigorous line is represented by light bars. In (D) the values for the control line are represented by the full line, whereas the values for the less vigorous line are represented by the dashed line.

Figure 3:
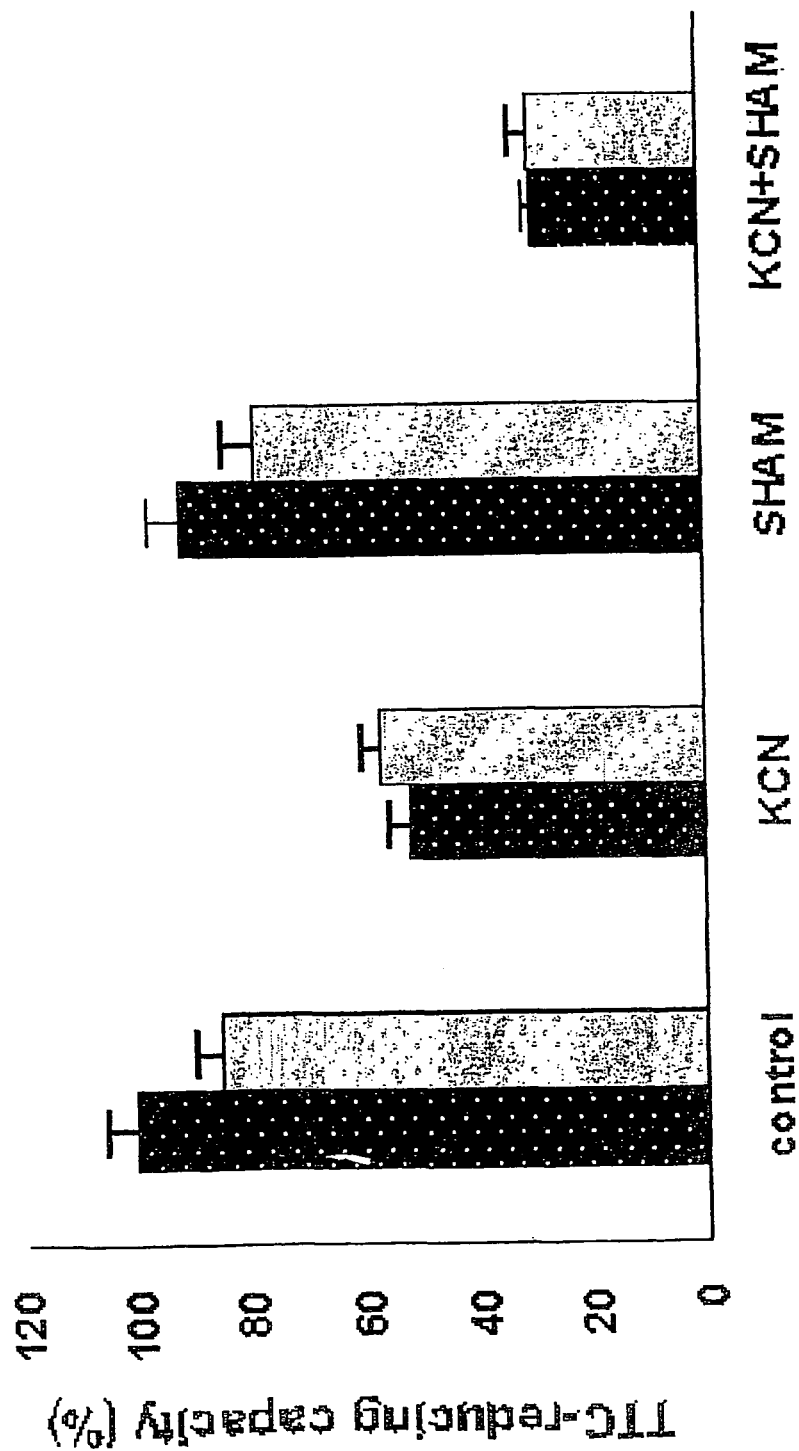

FIG. 3. Both the cytochromal and alternative respiratory pathways contribute to the reduction of TTC.

The experiments were done with two lines of *Brassica napus* (N90-740). The less vigorous line (light gray bars) (as scored in field trials, 90% yield versus control, and lower growth vigour) is identical to the control line (dark bars) but is transgenic for the pTA29: barnase gene (Mariani et al., 1990).

SHAM alone does not seem to have a major influence on the TTC reduction. This is probably due to an overflow of the electrons from the alternative to the cytochromal respiratory pathway (Millar et al., 1995; Kumar and Kumar Acharya, 1999). The TTC-reducing capacity that remains after the addition of both KCN and SHAM is due to the reduction of TTC by other enzymatic activities and superoxides (Møller et al., 1988; Moore and Siedow, 1991; Raap, 1983; Seidler, 1991; Sutherland and Learmonth, 1997; Able et al., 1998). Each value is the mean of three replicates with 150 explants per replicate. The error bars represent the standard error of the mean.

Figure 4:
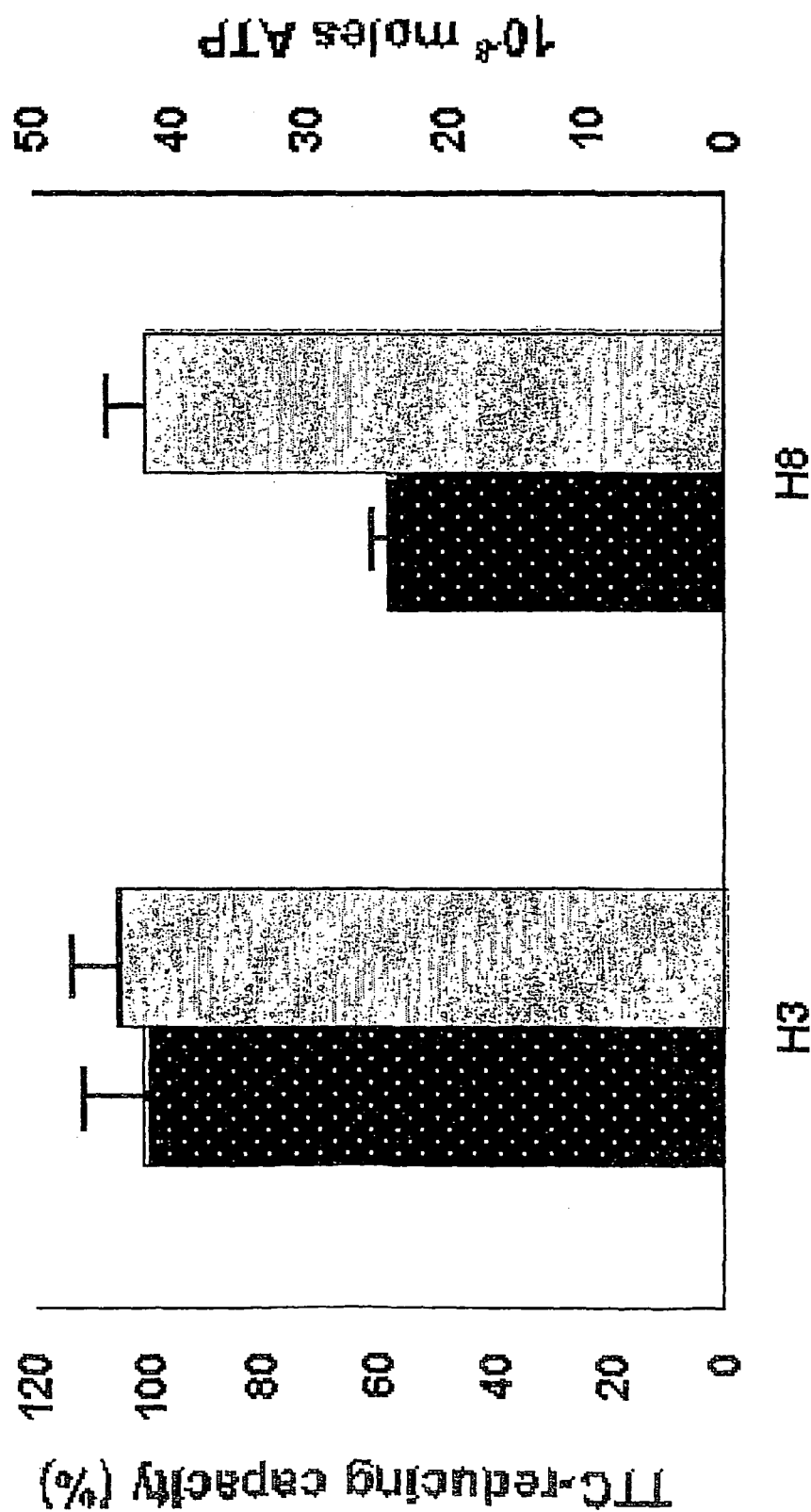

FIG. 4. There is no correlation between the TTC-reducing capacity and the ATP-content of five days cultured hypocotyl explants.

The hybrid lines H3 and H8 are two winter varieties of Brassica napus. H3 was scored in field trials as a good hybrid (128% yield versus control line), while H8 was scored as a poor performing hybrid (91% seed yield versus control). The error bars represent the standard error of the mean. The dark bars represent the values measured for TTC reduction (Y1), whereas the light gray bars represent the ATP-content (Y2).

Figure 5:
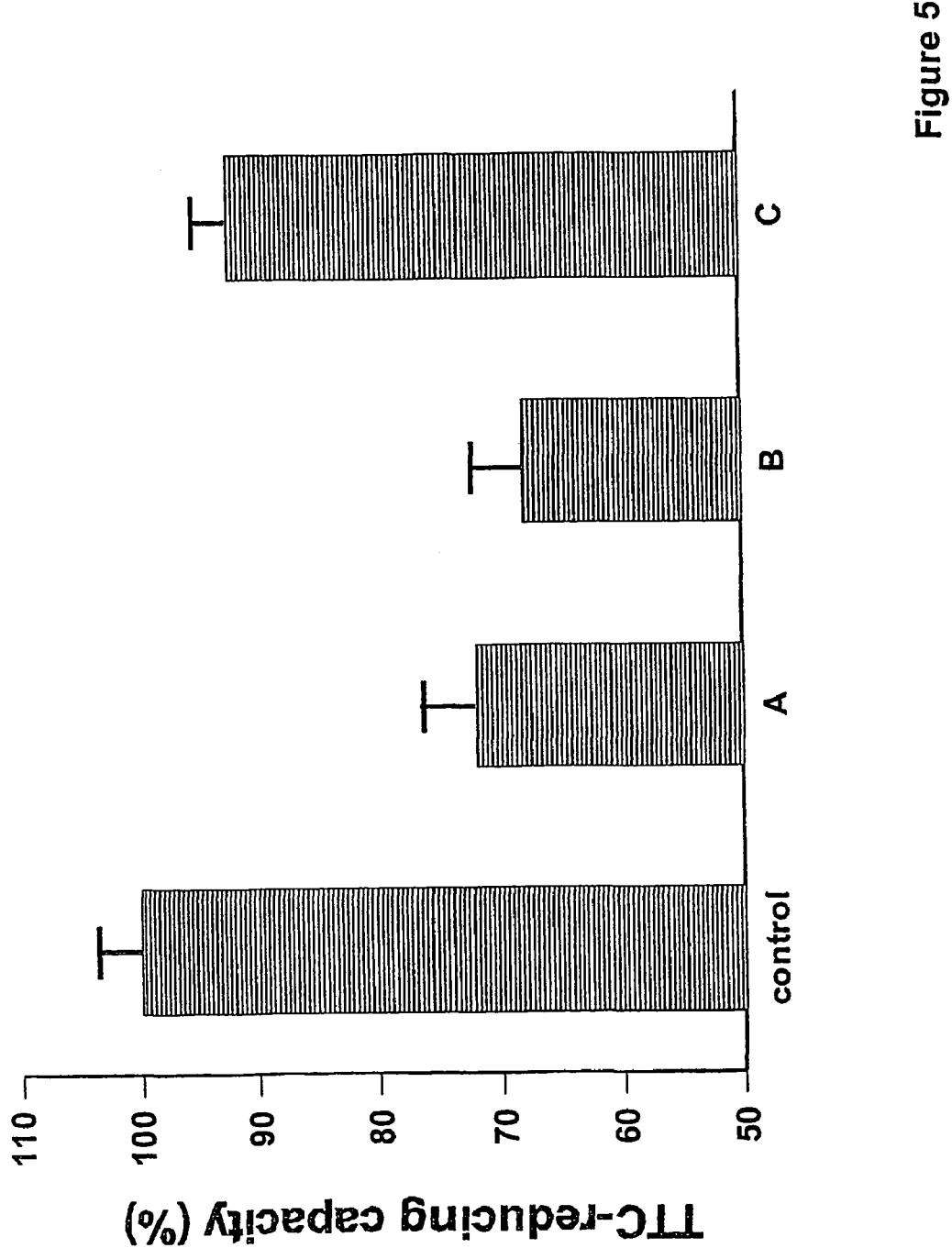

FIG. 5. The vigour assay can be used to identify lines affected in their vigour.

The *Brassica napus* lines indicated as A, B, and C are derived from the spring variety Drakkar. The latter was used as a control. The TTC-reducing capacities of the control line was set at 100%. Each value is the mean of three replicates. The error bars represent the standard error of the mean. When the yield of the control line is set at 100%, lines A, B and C have a yield of 86%, 84% and 95% respectively.

Figure 6:
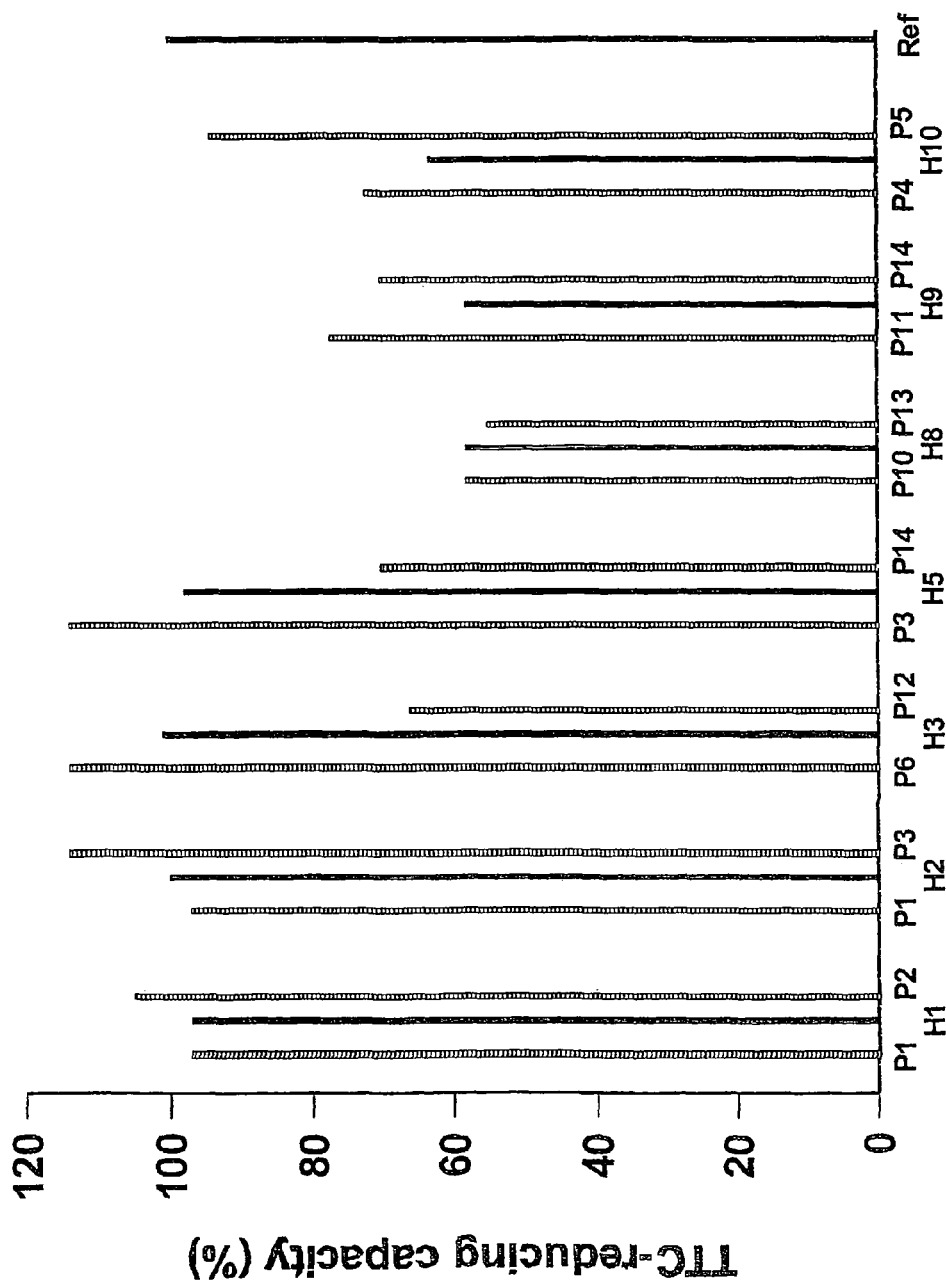

FIG. 6. The TTC-reducing capacity of *Brassica napus* parental lines and their hybrids. The parental lines have different genetic backgrounds (spring, winter, Chinese). The reference line is N90-740 of which the TTC-reducing capacity and yield was set to 100%. To obtain heterosis, two parental lines have to be combined of which at least one should have a high TTC-reducing capacity. Each value is the mean of three replicates with 150 explants per replicate. The standard error was less than 7% for each mean. Hybrid lines H1, H2, H3, H5, H8, H9 and H10 have yields of respectively 125%, 109%, 128%, 123%, 91%, 80% and 96%.

FIG. 7. (A) The vigour of hybrid lines can be measured by treating the explants for a prolonged time with acetylsalicylic acid. Four hybrid lines of *Brassica napus* (winter varieties) with different yield vigour were tested. The TTC-reducing capacity of the four lines was similar under control conditions. When 25 mg/l acetylsalicylic acid was added to the incubation medium, an inverse correlation was found between the yield vigour and the TTC-reducing capacity. The line N90-740 was used as standard for the TTC-reducing capacity and was set to 100%. Each value is the mean of three replicates with 150 explants per replicate. The error bars represent the standard error of the mean. The yield of lines 12, 13, 24 and 41 compared to the yield of N90-740 is respectively, 110%, 104%, 114% and 118%. Dark bars represent values obtained for 0 mg/l acetylsalicylic acid, light gray bars represent values obtained for 25 mg/l acetylsalicylic acid.

(B) The influence of 25 mg/l acetylsalicylic acid on the TTC-reducing capacity of 28 hybrid lines of *Brassica napus* (winter varieties) was measured. The 28 hybrids could be classified, versus a standard control line (set at 100%) on yield vigour in four classes: low (~100%), moderate (104-106%), high (110-114%) and very high (>118%). The boxes contain the 25th to 75th percentile of the data. The error bars beside the boxes represent the standard deviation with the indication of the mean.

(C) Correlation between the yield and the difference in TTC reducing capacity assayed on explants treated with acetylsalicylic acid or on control explants, for different *Brassica napus* lines.

(D) The TTC-reducing capacity at different concentrations of acetylsalicylic acid is different between the most and the less vigorous hybrids. The most vigorous hybrid lines show a decrease at 25 mg/l acetylsalicylic acid and again an increase at 50 mg/l acetylsalicylic acid. The lines are winter varieties with a very different genetic background. The TTC-reducing capacity at 0 mg/l acetylsalicylic acid is set at 100% for each line. Each value is the mean of three replicates with 150 explants per replicate. The error bars represent the standard error of the mean.

Dark bars represent values without acetylsalicylic acid, white bars are values in the presence of 25 mg/L acetylsalicylic acid, striped bars in the presence of 50 mg/L acetylsalicylic acid, and gray bars 100 mg/L acetylsalicylic acid.

Figure 8:
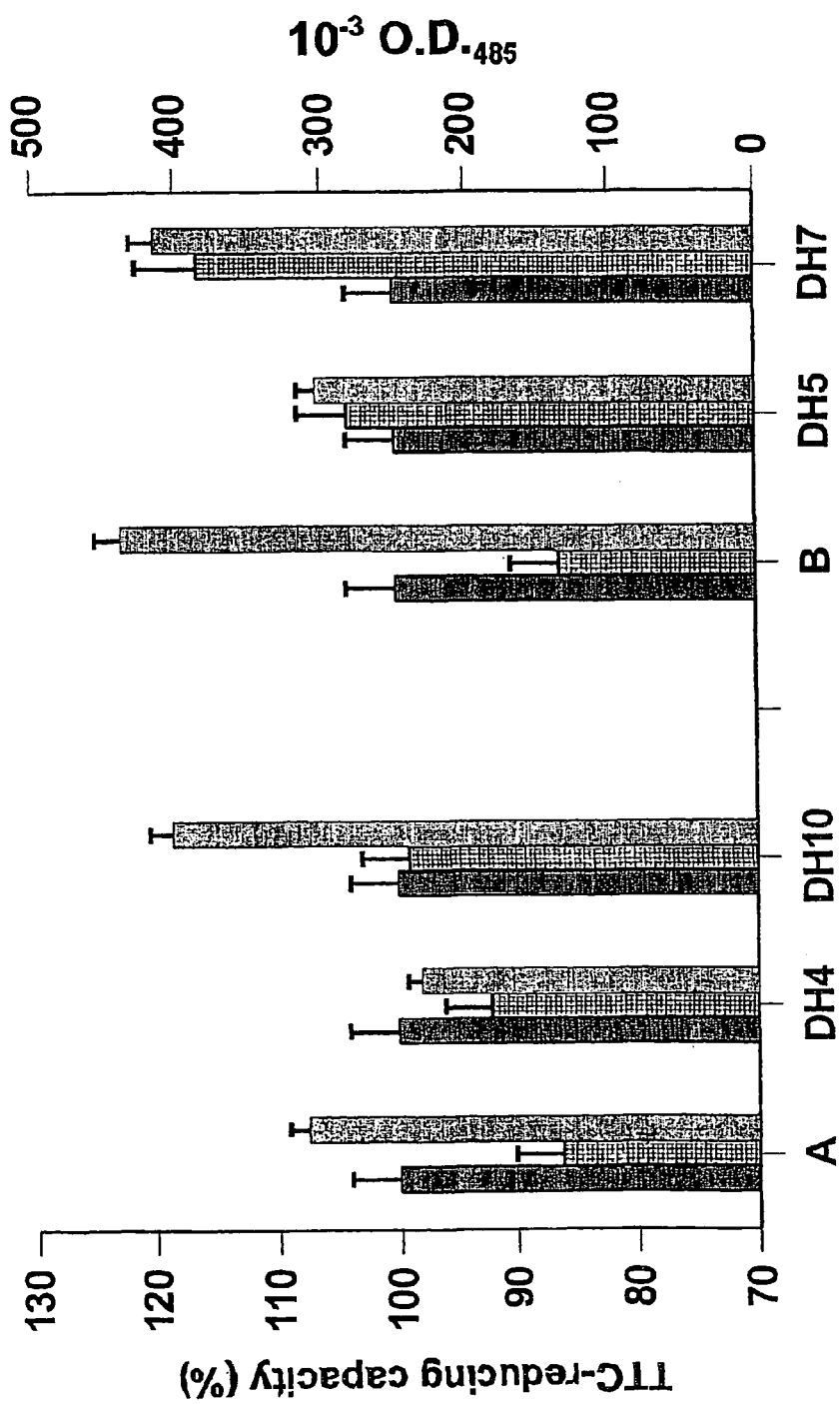

FIG. 8. Scoring parental lines of *Brassica napus* for their combining ability. Parental lines can be scored for their combining ability by scoring the degree of increase or decrease of the TTC-reducing capacity in the absence and presence of acetylsalicylic acid in the incubation medium. The lines A and B, that were identified in the breeding as excellent combiners, have a different genetic background. Also the genetic background from DH4, DH5, DH7 and DH10 is different from lines A and B. DH4, DH5, DH7 and DH10 are doubled haploids derived from the same parental line. Both the total reducing capacity at the control condition (0 mg/l acetylsalicylic acid) and the relative reducing capacities at control condition (set at 100%) and after acetylsalicylic acid treatment are plotted. The scored combining ability of DH4, DH5, DH7 and DH10 are based on the combining ability of DH4 and DH10 with A (respectively 110% and 118% yield scores of hybrids), and the combining ability of DH5 and DH7 with B (respectively 123% and 104% yield scores of hybrids). Each value is the mean of three replicates with 150 explants per replicate. The error bars represent the standard error of the mean. Combining abilities are scored as very good (A), moderate (DH4), good (DH10), very good (B), good (DH5) poor (DH7). Dark bars represent values obtained in the absence of acetylsalicylic acid, set at 100% (Y1), striped bars represent the TTC-reducing values (%) obtained in the presence of 25 mg/l acetylsalicylic acid. The light gray bars represent the absolute TTC reducing value (Y2) scored in the absence of acetylsalicylic acid.

DETAILED DESCRIPTION OF PREFERRED EMBODIMENTS

The invention is based on the surprising finding that heterosis in plants behaves as a dominant quantitative trait. Indeed, the inventors have found a correlation between the amount of electron flow in the mitochondrial transport chain under control conditions in the parent lines and the general fitness or vigour of the hybrid lines resulting from crosses between those parent lines, as determined by the different parameters scored during field trials. These findings allow to discard combinations of parent lines which will not yield hybrid lines with high heterosis and to proceed only with those parent lines which may yield hybrid lines with high heterosis effect.

Furthermore, an unexpected correlation could be found between the combining ability of parent lines and the change in the electron flow in the mitochondrial respiration chain under stress conditions compared to the electron flow in the mitochondrial electron transport chain under control conditions (without imposing stress conditions). These findings allow to predict the combinations of parent inbred lines which will yield hybrid lines with high heterosis effect.

Finally, an improved vigour assay based on the change in the electron flow in the mitochondrial respiration chain under stress conditions imposed by incubation in the presence of salicylic acid or derivates, compared to the electron flow in the mitochondrial electron transport chain under controlled conditions allows a better discrimination of the resulting plant lines according to their agronomical performance.

Thus, in a first embodiment, the invention provides a method for determining good parental plant lines, preferably inbred lines which upon crossing with other parent plant lines, preferably inbred plant lines is capable of yielding a hybrid plant line with high heterosis. This method comprises the steps of:

a) culturing explants of each of the parent inbred plant line of the collection under conditions which activate the metabolism in the explants;

b) measuring the electron flow in the mitochondrial electron transport chain in the explants, relative to the electron flow in the mitochondrial electron transport chain in the explants from a reference plant line of the same species, preferably of the same variety; and c) selecting the parent inbred lines which have the greatest relative amount of electron flow in the mitochondrial electron transport chain.

As used herein, "heterosis effect" or "hybrid vigour" is used to refer to the superiority of heterozygous genotypes with respect to one or more characters, particularly with regard to a character of interest such as yield, in comparison with the corresponding homozygotes.

Preferably, the explants are hypocotyl explants, but other explants such as callus, shoots, leaf disks or whole leaves may be used to the same effect. It is further preferred that the explants should be derived from sterile in vitro grown material that has a high respiration rate or an active metabolism. This may be achieved by culturing or incubating the explants first on a medium comprising a suitable carbohydrate, such as sucrose, to enhance the respiration rate or metabolism. More preferably, explants are cultured on a callus inducing medium for a time sufficient to activate the metabolism, particularly for about 0 to 10 days, preferably for about 4 to 6 days, particularly for about 5 days. Preferably, the callus-inducing medium comprises sucrose, particularly about 2% to 3% w/w. Preferred temperature ranges for culturing the explants are about 24 to 25° C.

Preferably, the electron flow in the mitochondrial electron transport chain is determined by measuring the capacity of the explant to reduce 2,3,5 triphenyltetrazolium chloride (TTC). Although it is believed that for the purpose of the assays defined here, TTC is the most suited substrate, other indicator molecules, such as MTT (3-(4,5-dimethylthiazol-2-yl)-2,5 diphenyl-2H-tetrazolium), can be used to measure the electron flow in the mitochondrial electron transport chain downstream of the "ubiquinone pool".

In another embodiment of the invention, an improved method for determining the vigour of a plant, i.e. for determining in vitro the agronomical fitness of a plant line is provided comprising:
a) culturing a population of explants of a parent inbred plant line under conditions which activate the metabolism in the explants;
b) incubating a first part of the cultured explants for about 18 hours in a buffer comprising about 25 mM K-phosphate and about 2 to 3% sucrose
c) incubating a second part of the cultured explants, preferably for about 18 hours in a buffer comprising preferably about 25 mM K-phosphate and about 2 to 3% sucrose and further comprising a salicylic acid derivative capable of generating oxidative stress in plant cells incubated in a solution of said salicylic acid derivative, preferably in a concentration of about 25 mg/L;
d) measuring the electron flow in the mitochondrial electron transport chain in said first and second part of the population.

Explants from vigourous plants have a lower electron flow in the mitochondrial electron transport chain when assayed under conditions comprising the stress with the salicylic acid derivative then when assayed under control conditions without such imposed stress. The larger the reduction in electron flow under stress conditions, the more vigourous the plant or plant line from which the explants were derived. When the electron flow is measured by TTC reducing capacity, and the difference) is expressed by subtracting the data obtained from the second part of explants (under stress conditions) from the data obtained from the first part of explants, vigourous plants should exhibit a negative score. The more negative the score, the more vigourous the plant. The $\Delta$ TTC reducing capacity may also be expressed as a percentage of the TTC reducing capacity under control conditions (mean TTC reducing capacity under stressed conditions—mean TTC reducing capacity under control conditions/mean TTC reducing capacity under control conditions). The thus obtained figure should preferably be at least about −10% but may be as much as about −50%.

This method may be applied for selecting a plant line having the highest growth and yield vigour from a collection of plant lines from the same species, preferably from the same variety. It may also be used for the identification of physiological conditions that affect the fitness of the plants (increase or decrease) or to discriminate mutant plants, cells or cell lines from wild-types.

It goes without saying that the preferred method for determining the vigour as described above may be varied within limited ranges while retaining the improved results. Preferably the buffer is a K-phosphate buffer in a concentration of about 25 mM, but concentrations of about 5 mM to about 40 mM may be used to similar effect, as well as other buffers. Preferably the carbon source is sucrose in a concentration of about 2 to about 3% w/v but concentration ranges of about 1 to 4% may be used to the same end, as well as other carbon sources which can be used by the plants or explants as energy sources. Preferably, the salicylic acid derivative capable of generating oxidative stress in plant cells is acetylsalicylic acid particularly in a 25 mg/L concentration range, but concentrations as low as about 5 mg/L or as high as about 50, particularly ranging from about 20 to about 40 mg/L may also be used.

Depending on the plant species assayed, some variation in the concentration ranges particularly those of the salicylic acid derivative may be varied to obtain optimum results. To identify the optimum concentration of the salicylic acid derivative, explants from a number of reference plants or plant lines with a known yield as determined in vivo, preferably in field trials, are subjected to the above described assays using a number of concentrations of a salicylic acid derivative capable of generating oxidative stress in a plant cell, preferably within the range of 5 to 50 mg/L particularly within the range of 20 to 40 mg/L. The optimum concentration of salicylic acid for any given plant may be determined as the concentration where the largest difference in TTC reducing capacity is obtained. The known yield of plant lines should be correlated with the $\Delta$TTC reducing capacity (as defined above). The ranges of buffer concentrations, temperature and incubation time may be optimized to obtain the highest metabolic activation, as reflected by the highest TTC reducing capacity.

To avoid any differences due to physiological conditions of the growing plants from which the explants are derived, seeds to obtain the plants for the assay may be primed before sowing. This may be achieved e.g. by shaking seeds for about 20 hours in sterile tap water containing 500 mg/l ticarcillin disodium and selecting only those seeds that start to germinate.

The above described methods may further be used in the selection of parent lines for the production of hybrid plants. In other words, parent lines with good combining ability may be predicted based on the following method which can be performed in vitro. Thus, in another embodiment of the invention a method for producing a hybrid plant line is provided, comprising the steps of:
a) assaying a collection of inbred lines of interest by
i) culturing a population of explants (preferably isolated hypocotyls) of each of the parent inbred plant line of the collection under conditions which activate the metabolism in the explant;
ii) measuring the electron flow in the mitochondrial electron transport chain in the population of explants, relative to the electron flow in the mitochondrial electron transport chain in population of explants from a reference plant line of the same species, preferably of the same variety, preferably by determining the TTC reducing capacity;

b) selecting a parent inbred line which has a high relative amount of electron flow in the mitochondrial electron transport chain when compared to other inbred lines from the collection;

c) crossing the selected inbred line with another inbred line;

d) collecting seed from the crossed selected inbred line and optionally, planting and growing the seed to obtain the hybrid plants.

For more accurate prediction of the combining ability of at least one parent line, both assay methods as described may be combined, and the parent line or lines should have a good score in both tests. The invention thus also provides a method for producing a hybrid plant line, comprising the steps of:

a) assaying a collection of inbred lines of interest by
    i) culturing a population of explants (preferably hypocotyls) of each of the parent inbred plant line of the collection under conditions which activate the metabolism in the explant;
    ii) measuring the electron flow in the mitochondrial electron transport chain in the population of explants, relative to the electron flow in the mitochondrial electron transport chain in population of explants from a reference plant line of the same species, preferably of the same variety;

b) assaying the collection of inbred lines of interest by
    i) culturing a population of explants of each of the parent inbred plant lines of the collection under conditions which activate the metabolism in the explants;
    ii) incubating a first part of the each of the populations of cultured explants, preferably for about 18 hours in a buffer preferably comprising about 20 to 30, particularly about 25 mM K-phosphate and about 2 to 3% sucrose;
    iii) incubating a second part of each of the populations of the cultured explants for about 18 hours in a buffer, preferably comprising about 20 to 30, particularly about 25 mM K-phosphate and about 2 to 3% sucrose and further comprising a salicylic acid derivative capable of generating oxidative stress in plant cells incubated in a solution of the salicylic acid derivative, preferably in a concentration of about 20 to 30 mg/L, particularly about 25 mg/L;
    iv) measuring the electron flow in the mitochondrial electron transport chain in each of the first and second parts of the populations;

c) selecting a parent inbred line from the collection which has a high relative amount of electron flow in the mitochondrial electron transport chain when compared to other inbred lines from that collection and which has a large negative difference between the measured electron flow in the mitochondrial electron transport chain between the second and the first part;

d) crossing the selected inbred line with a second inbred line; and e) collecting seed from the crossed selected inbred line and optionally planting and growing the seed to obtain the hybrid plants.

In a preferred embodiment, both parent lines, particularly parent inbred lines have been selected as performing good in both assays.

The methods of the invention are particularly suited for Brassicaceae plants, particularly oilseed rape, but may be used to similar ends in other plants such as lettuce, tobacco, cotton, corn, rice, wheat, vegetable plants, carrot, cucumber, leek, pea, melon, potato, tomato, sorghum, rye, oat, sugarcane, peanut, flax, bean, sugarbeets, soya, sunflower, ornamental plants.

It has also been found that the methods described herein may be used to classify individual plants of a particular plant variety or plant line according to their agronomical fitness and yield vigour.

The following non-limiting Examples describe the particular embodiments of the invention. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. Specific experimental procedures used in the described Examples are outlined below:

Media and Buffers

Sowing medium (medium 201): half-concentrated Murashige and Skoog salts (Murashige and Skoog, 1962), 2% sucrose, pH 5.8, 0.6% agar, 250 mg/l ticarcillin disodium (Duchefa, Netherlands).

Callus inducing medium A2S3: Murashige and Skoog medium (Murashige and Skoog, 1962), 0.5 g/l Mes (pH 5.8), 3% sucrose, 40 mg/l adenine-SO4, 0.5% agarose, 1 mg/l 2,4-D, 0.25 mg/l NAA, 1 mg/l BAP, 250 mg/l ticarcillin disodium (Duchefa, Netherlands).

Incubation medium: 25 mM K-phosphate buffer pH5.8, 2% sucrose, 1 drop Tween20 for 25 ml medium. The phosphate buffer and sucrose were autoclaved separately. When acetylsalicylic acid was added, a stock solution of 10 mg/ml at a pH5.8 was used.

Reaction buffer: 50 mM K-phosphate buffer pH7.4, 10 mM 2,3,5-triphenyltetrazoliumchloride (=TTC) (ICN, Ohio, USA), 1 drop Tween20 for 25 ml buffer. The majority of the dissolved oxygen was removed until a final oxygen concentration of the reaction buffer was about 2 mg/l. For quantifying the contribution of the cytochromal and/or alternative respiration, 1 mM KCN and/or 10 mM salicylhydroxamic acid (SHAM) were added.

Vigour Assay

Sterilization of seeds and growing of the seedlings: Seeds were soaked in 70% ethanol for 2 min, then surface-sterilized for 15 min in a sodium hypochlorite (with about 6% active chlorine) containing 0.1% Tween20. Finally, the seeds were rinsed with 1 l of sterile distilled water. Seeds were put in 1 l vessel (Weck, Germany) containing about 75 ml of sowing medium (10 seeds/vessel). Alternatively, the seeds were put in "in vitro vent containers" (Duchefa, The Netherlands) containing 125 ml of sowing medium (12 seeds/container). The seeds were germinated at 24° C. and 20 µEinstein/$s^{-1}m^{-2}$ with a day length of 16 h. The line N90-740 was included as standard.

Priming of the seeds: If the seed quality of the tested lines was different, then the seeds were primed. This was done by shaking the sterilized seeds for about 20 hours in sterile tap water containing 500 mg/l ticarcillin disodium (Duchefa, Netherlands). Only the seeds that started to germinate (radicle protruded) were sown.

Preculture of the hypocotyl explants: 12 days after sowing, the hypocotyls were cut in about 7 mm segments (about 5 explants/seedling). The hypocotyl explants (25 hypocotyl explants/Optilux Petridish, Falcon S1005, Denmark) were cultured for 4-5 days on medium A2S3 at 25° C. (at 20 µEinstein/$s^{-1}m^{-2}$). 150 hypocotyl explants/line/condition were used. An extra 150 hypocotyl explants were cut, these were used as blank in the TTC-reaction (see later). Incubation step: After these 4-5 days, 150 hypocotyl explants/line/condition were transferred to an Optilux Petridish (Falcon S1005, Denmark) containing 25 ml of incubation medium, including an extra plate with the 150 hypocotyl explants that were cut at the start of the experiment (see above). This plate was used as blank (see later). The plates were incubated for about 18 hours at 24° C. in the dark.

TTC-assay: The batches of 150 hypocotyl explants were transferred to 50 ml Falcon tubes and washed with reaction buffer without TTC (2,3,5-triphenyltetrazolium chloride). 25 ml-30 ml of reaction buffer (containing 10 mM TTC) was added per tube. For the blank no TTC was added (for measuring the background absorption). For this the extra 150 hypocotyl explants were used (see above). The explants were submerged, but no vacuum infiltration was done. The tubes were incubated upside down for one hour in the dark at 25° C. (no end reaction!). After the reaction, the hypocotyls were washed with deionized water. The water was removed and the material was frozen −70° C. for 30 min. After thawing, 50 ml of technical ethanol was added per tube. The reduced TTC-H was extracted by shaking for 1-1.5 hours. The absorption of the extract was measured at 485 nm: O.D. 485 (TTC-H)= (O.D. 485+TTC)−(O.D. 485 without TTC). The TTC-reducing capacity of the line N90-740 was used as reference and was set at 100%.

Quantification of ATP in Hypocotyl Explants

The quantification of ATP was mainly done as described by Rawyler et al. (1999).

Material: hypocotyl explants cultured for 5 days on A2S3 medium.

ATP extraction: The hypocotyl explants were frozen with liquid nitrogen (in batches of 50 explants). Frozen hypocotyls were grinded with a mortar and pistil in 6 ml of 6% perchloric acid. The extract was centrifuged at 24,000 g (Sorvall, SS34 rotor at 14,000 rpm) for 10 min. at 4° C. The supernatant was neutralized with 5M $K_2CO_3$ (350 µl of 5M $K_2CO_3$ to 3 ml of supernatant). The $KClO_4$ was removed by spinning as described before.

Quantitative bioluminescent determination of ATP: The ATP bioluminescent assay kit from Sigma was used (FL-AA). The luminescence was measured with the TD-20/20 luminometer of Turner Designs (Sunnyvale, USA).

Quantification of the Superoxide Production by the Hypocotyl Explants

The formation of superoxides by the explants was quantified by measuring the reduction of XTT (sodium, 3'-{1-[phenylamino-carbonyl]-3,4-tetrazolium}-bis(4-methoxy-6-nitro) benzene-sulfonic acid hydrate) as described (Sutherland and Learmonth, 1997; Able et al., 1998). After the incubation step of the vigour assay, the incubation medium was replaced by reaction buffer containing 1mM XTT instead of TTC (20 ml reaction buffer for 150 hypocotyl explants). The formation of XTT formazan was followed by measuring the absorbance of the medium at 470 nm.

EXAMPLE 1

Optimizing Vigour Assay Variables for a Given Plant Species

Figure 1:
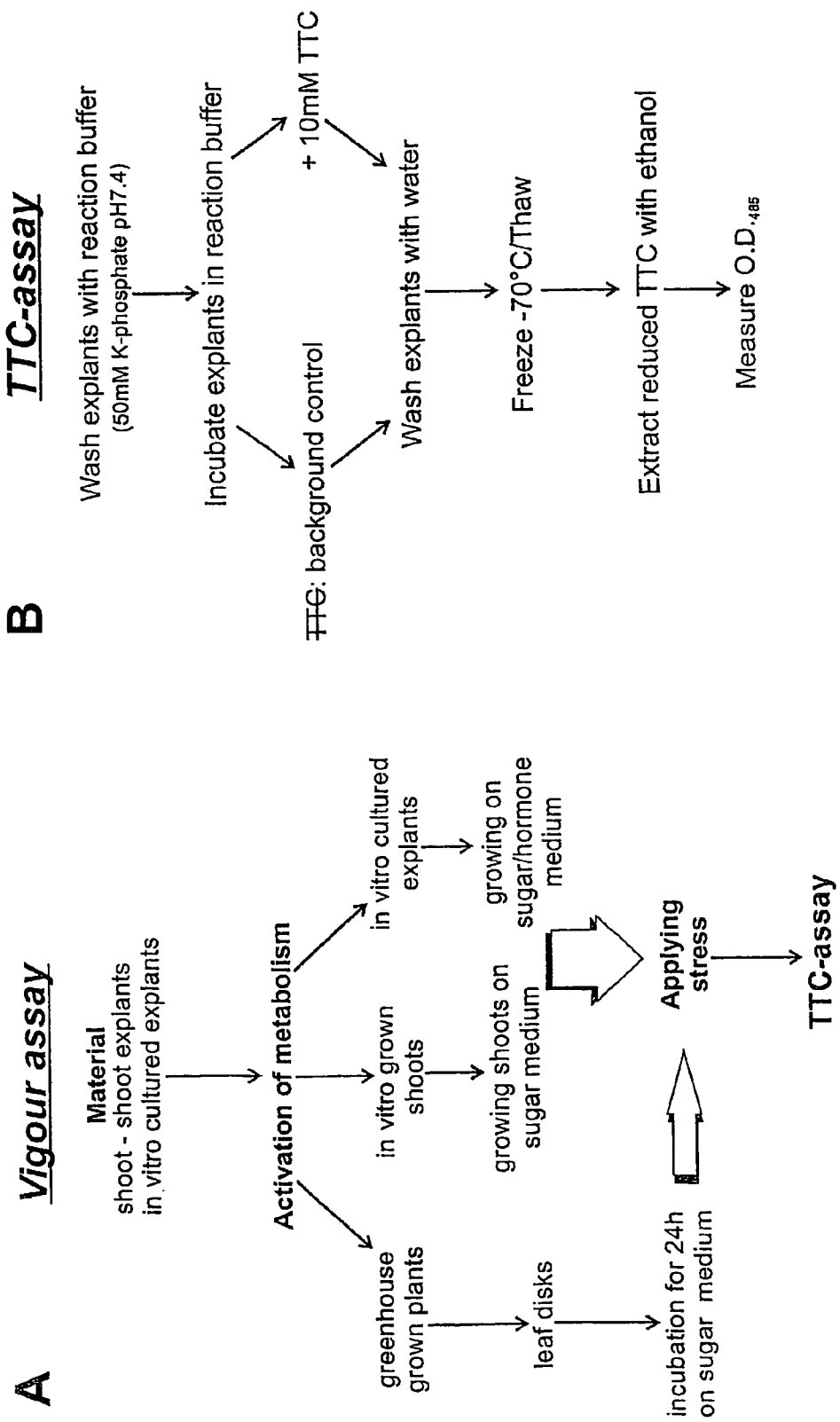
FIG. 1. Flow charts of the vigour assay (a) and the TTC-assay (b).

The vigour assay is generally outlined in FIG. 1. It is preferred to start from sterile in vitro grown material that has a high respiration rate. E.g. leaf explants from greenhouse-grown plants should not be used directly but first be incubated with sucrose to enhance the respiration. The different components of the system, which are of importance for the reliability of the assay, were analysed using two lines derived from the spring variety N90-740 of *Brassica napus*. One of the lines had a seed yield comparable to the original N90-740 line and is indicated as the control line. The second line had been determined by field trials as having a lower seed yield (about 90% of the control line) and is indicated in FIG. 2 as 'less vigorous' (lower seed yield, 90%, and less vigorous growth). Except for the specific variables that were studied, the vigour assay was done as described above (see also FIG. 1B).

Culture Conditions of the Hypocotyl Explants

Figure 2A:
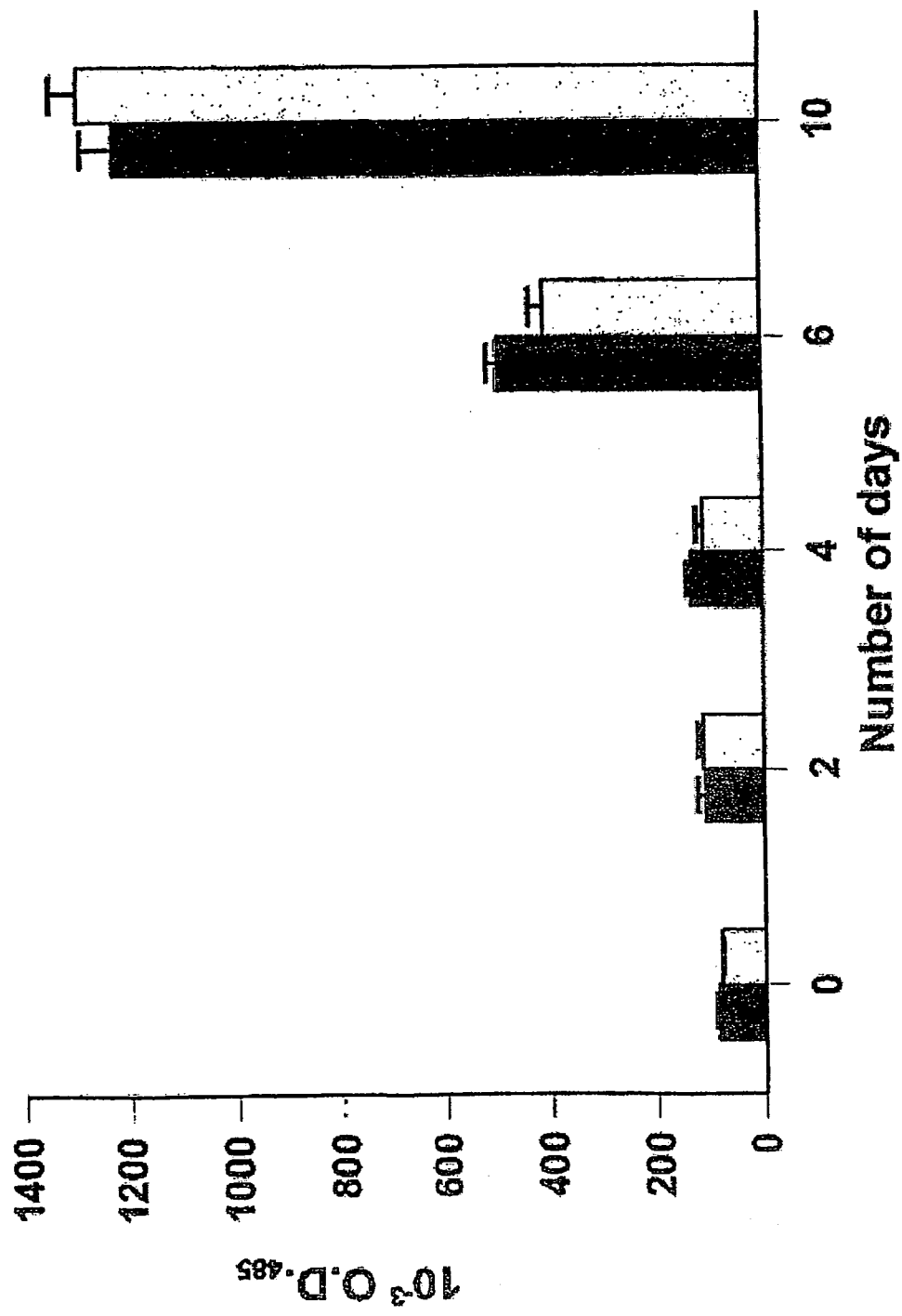
FIG. 2. Variables that influence the quality of the vigour assay. A. Influence of pre-culturing on growth medium. B. Influence of the temperature of the preculture. C. Influence of the incubation step. D. Influence of the concentration of K-phosphate in the incubation medium.

Freshly isolated hypocotyl explants have a low metabolic activity and respiration rate: very low malate dehydrogenase activity and almost no TTC-reducing capacity. To activate metabolism, the explants were cultured for 0 to 10 days on callus inducing medium. The TTC-reducing capacity was determined before incubation and after respectively 2, 4, 6, and 10 days of culture. The results are shown in FIG. 2A. The clearest relative difference between the control and less vigorous line was measured after 4 to 6 days of culture. Often the differences disappear after 10 days of culture. A period of five days on callus inducing medium was chosen as the standard activation time.

Figure 2B:
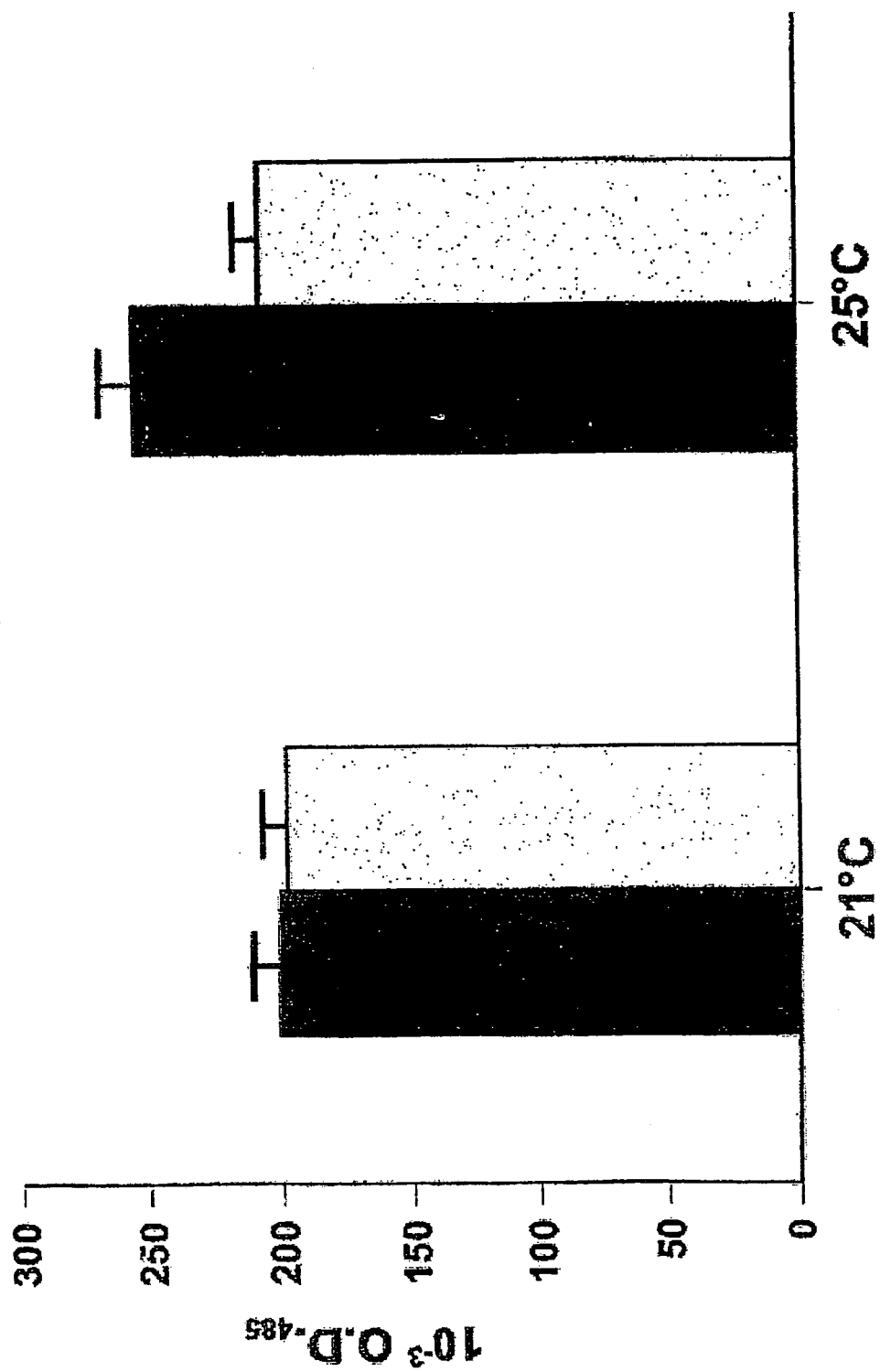

Not only the duration of the culture period may influence the assay, but also the culture conditions in general will determine how and at which degree the metabolism will be activated. In optimizing the vigour assay several variables in the culture conditions such as carbon source, carbon concentration, and temperature were evaluated. Sucrose (2-3%) was the best carbon source, while a culture temperature of 24-25° C. was found to be better than lower temperatures (FIG. 2B).

Incubation Step in K-Phosphate Buffer

Figure 2C:
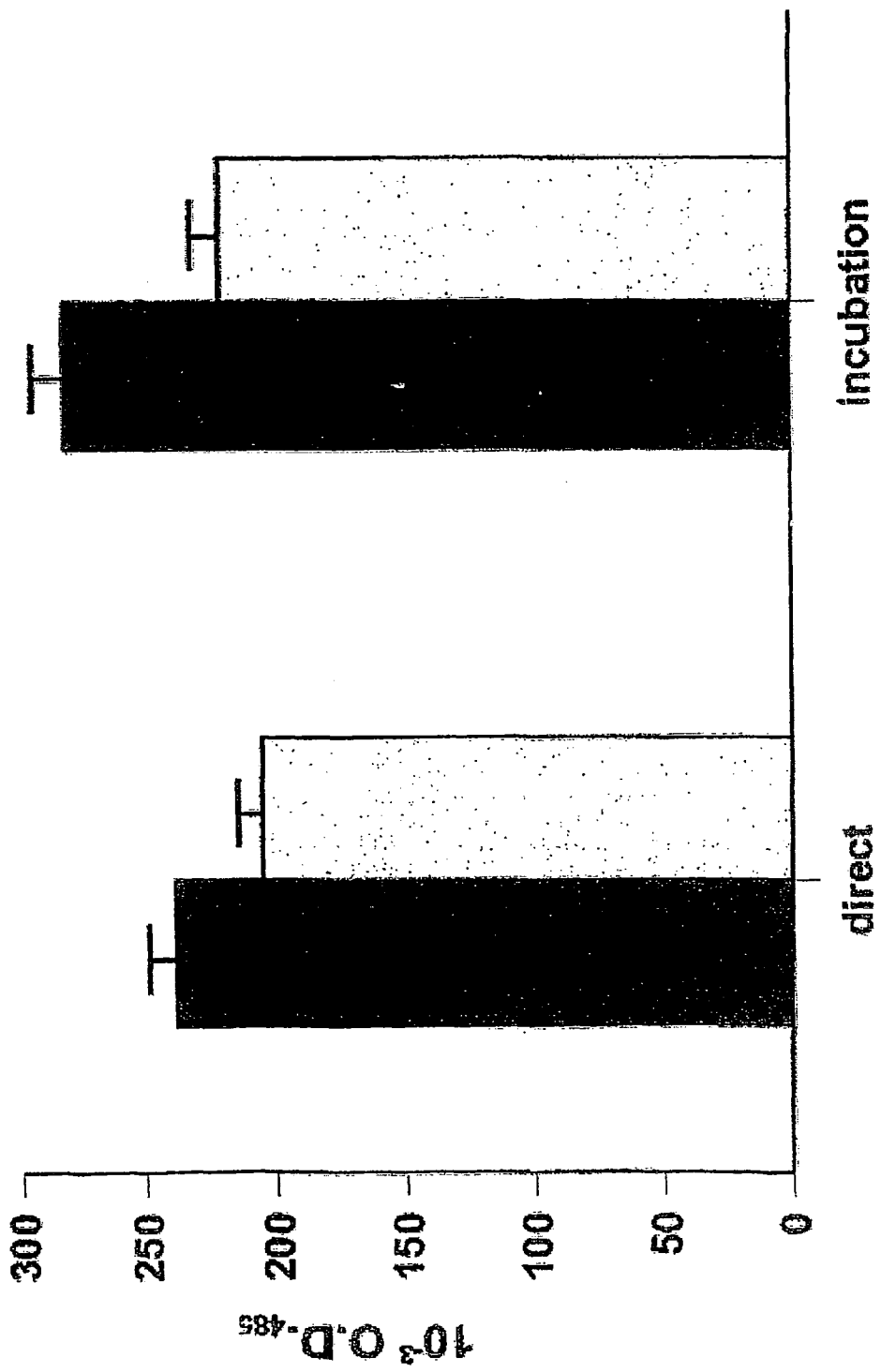

Typically, the explants are incubated for about 18 hours in K-phosphate buffer containing 2-3%سucrose. As is illustrated in FIG. 2C, the difference in TTC-reducing capacity between the two lines with different vigour was more pronounced when the hypocotyl explants were incubated for about 18 hours in K-phosphate buffer. When the TTC-assay was done directly on the 5 days cultured explants the difference was less clear. Moreover the incubation step allows addition of compounds such as stress inducers and enzyme inhibitors to the buffer.

Figure 2D:
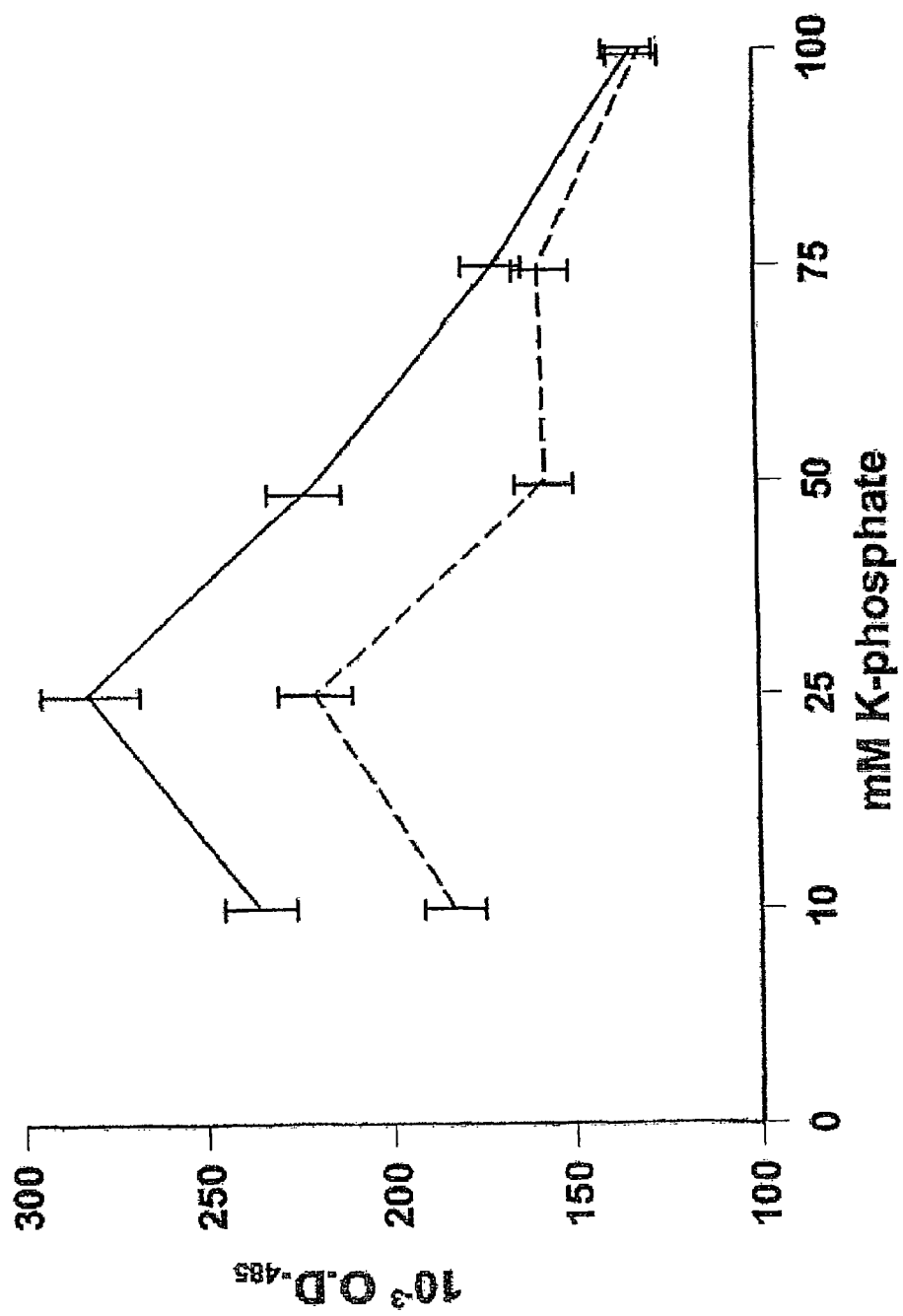

In FIG. 2D the TTC-reducing capacity of the control and less vigorous line in relation to the K-phosphate concentration of the incubation medium is depicted. Incubation in 25 mM K-phosphate resulted in the highest values and the largest differences between the two lines.

The K-phosphate buffer and sucrose should be autoclaved separately. For reasons that are not understood, autoclaving both together may have an adverse effect on the vigour assay.

EXAMPLE 2

Physiological Studies

Both the Cytochromal and Alternative Respiration Contribute to the Reduction of TTC Recently, it has been shown that TTC is reduced by mitochondrial dehydrogenases, particularly of Complex I. Moreover, the efficiency of the formazan formation depends on the activity of cytochrome oxidase which determines the aerobic state (Rich et al., 2001). In addition to the cytochromal respiratory pathway, an alternative respiratory pathway exists in plants. To analyze the relative importance of the cytochromal respiration versus the alternative respiration in the reduction of TTC, the hypocotyl explants were put after the incubation step in reaction buffer containing 1 mM KCN and/or 10 mM SHAM. KCN inhibits the cytochromal pathway at complex IV (cytochrome oxidase), while SHAM inhibits the alternative respiratory pathway (alternative oxidase). Kumar and Kumar Acharya (1999) described the addition of 2,6-dichloro-phenol indophenol to prevent overflow of the electrons between the cytochromal and alternative respiratory pathways when KCN and SHAM are used as inhibitors. However, 2,6-dichloro-phenol indophenol interfered with the TTC-assay (data not shown), for this reason 2,6-dichloro-phenol indophenol was not added to the reaction buffer. The results of these experiments are summarized in FIG. 3. Although the obtained values do not present the correct contribution of the cytochromal and alternative respiratory pathways, they show that both the cytochromal and alternative respiration contribute to the reduction of TTC. The TTC-reduction that remains in the presence of both KCN and SHAM, about 25%, is probably due to other pathways (Møoller et al., 1988; Moore and Siedow, 1991) and the presence of superoxides (Raap, 1983; Seidler, 1991; Sutherland and Learmonth, 1997; Able et al., 1998).

The Vigour of a Plant Line is not Related to the ATP Content

The amount of TTC that is reduced in a certain time period reflects the intensity of the mitochondrial electron transport system. Therefore, it could be that the vigour of a plant line could be measured by directly quantifying the ATP content of the shoots or explants. Such an assay would be convenient and quantitative.

Two lines of *Brassica napus* (winter varieties) with a very different yield vigour (128% for H3, and 91% for H8) were chosen as starting material. The vigour assay was performed as described but besides a TTC-assay, the ATP content of the hypocotyl explants was determined. FIG. 4 clearly shows that there is no correlation between the vigour of the plant line and the ATP content: in both lines the ATP content is very similar.

EXAMPLE 3

Influence of the Quality of the Seedlot on the Vigour Assay for *Brassica Napus* and Neutralization of the Seed Quality Factor by Seed Priming Plants from the same genotype and grown at identical conditions but derived from different seed batches can vary a lot in vigour. This variation in vigour is largely determined by the quality of the seedlot from which the plants originated (Larsen et al., 1998; Strydom and Van de Venter, 1998). This phenomenon is well known by seed companies, who test the seedlots for their quality (read percent germination and the growth rate of the seedlings at optimal and suboptimal conditions) before these are introduced into the market.

To test the influence of the quality of the seedlot on the vigour assay for *Brassica napus*, seedlots of two commercial lines were used as starting material. From each line two seedlots with a high germination efficiency (97%) but with a different seedling vigour, as judged in the seed quality tests (germination rate at 12° C. and 23° C.), were chosen. From the results of the vigour assays summarized in Table I it seems that the vigour assay may be influenced by the quality of the seedlot although to a limited extent. When the seeds were primed before sowing the vigour scores were no longer influenced by the quality of the seedlot (Table I).

TABLE I

The influence of the quality of the seedlot and the effect of seed priming on the vigour assay of *Brassica napus*

|  | line A | | line B | |
| --- | --- | --- | --- | --- |
|  | lot 1 | lot 2 | lot 1 | lot 2 |
| Seed quality test (%)[a] | 95 | 72 | 97 | 88 |
| Vigour Control (%)[b,c] | 100 ± 3 | 92 ± 6 | 100 ± 2 | 94 ± 4 |
| Vigour primed seeds (%)[c] | 100 ± 2 | 101 ± 3 | 103 ± 3 | 99 ± 4 |

[a] as judged by scoring germination at 12° C. and 23° C.
[b] per line, the seedlot with the highest score was set at 100% in the control condition (seeds not primed)
[c] values represent the mean ± standard error of the mean Seedlots of a different quality (about same germination rate but giving rise to seedlings with a different vigour as reflected in growth rate) from two commercial varieties (line A and line B) were used as starting material. The vigour assay was done on seedlings derived from non-treated and primed seeds. The priming was done as described in 'Materials and Methods'.

EXAMPLE 4

The Integration of the Various Vigour Assay Methods in *Brassica napus* Breeding Identification of Lines Affected in Their Vigour In the previous Examples, two lines were used to initially set up the vigour assay. In this way optimal conditions to discriminate these two lines on the base of their TTC-reducing capacity could be defined. The experiment in which the lines H3 (128% yield vigour) and H8 (91% yield vigour) were used to study the TTC-reducing capacity in relation to the total ATP content, already showed that the correlation between the yield score and the TTC-reducing capacity also holds true for these two lines. To obtain further confirmation for this correlation, three more lines that were well-characterized in field trials, were selected. From FIG. 5 it appears that the lines with a poor field performance (lines A and B) have a low TTC-reducing capacity compared to the control line and line (C). This implies that within a variety, vigour is correlated to the total TTC-reducing capacity: more vigorous lines having a higher TTC-reducing capacity than less vigorous lines.

The TTC-Reducing Capacity of the Parental Lines Influences the Vigour of Their Hybrids From the above described experiments it appears that the vigour assay can be used to identify weaker lines within a variety. This is of interest for biotechnology and breeding e.g. to test in an early phase whether the expression of a certain transgene in a particular line could have an adverse effect on the overall vigour of the plant. The vigour assay would have a high added value if it would allow to identify lines with an increased vigour, and to compare lines with a very different genetic background. However, each variety has its own intrinsic TTC-reducing capacity in the vigour assay (see e.g. FIG. 6). It is expected that within a variety, lines could be compared, but the more the varieties are genetically diverse the less the comparison of the total TTC-reducing capacities reflects their vigour.

Figure 7A:
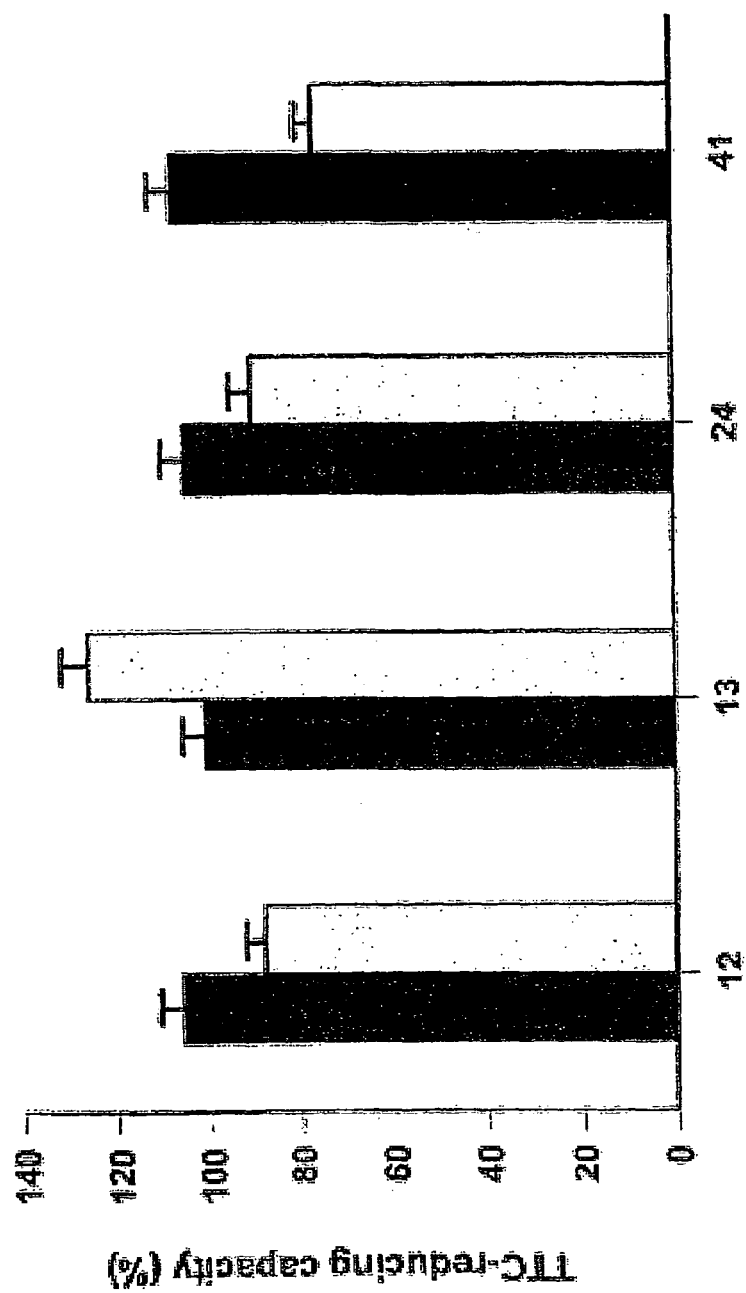
Figure 7B:
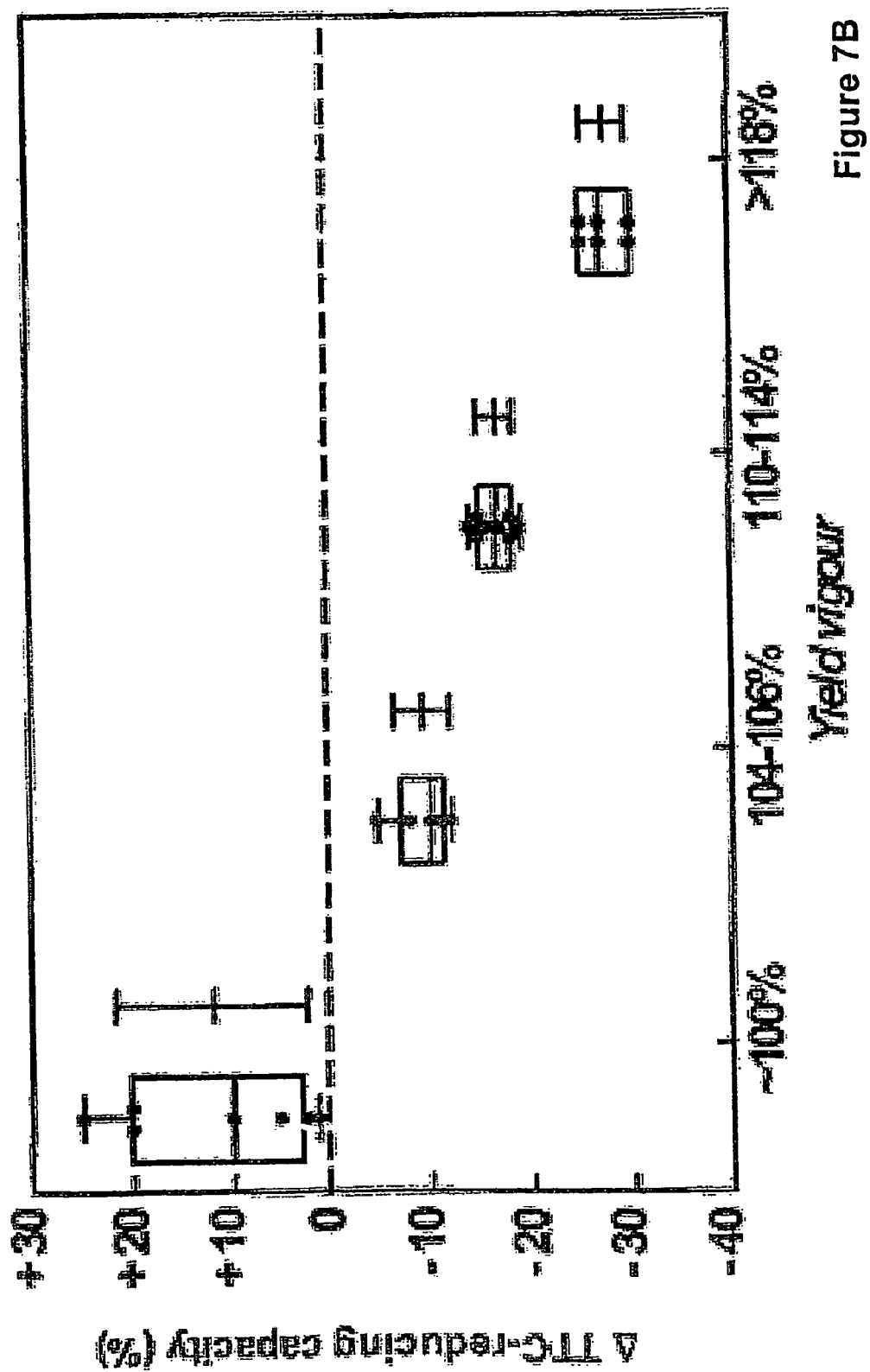

To test whether the vigour assay could be used in breeding programs to evaluate lines with a different genetic background, parental lines and their hybrids, with a different vigour as scored in field trials (mainly scored on seed yield), were analysed in the vigour assay. The variety N90-740 was used as reference line and was set at 100% for TTC reducing capacity. FIG. 6 represents an example of the results obtained from such analyses. The following information can be obtained from these data. For example, the lines P3 and P6 have the highest TTC-reducing capacity and were scored by the breeders as the best parental lines. Well performing hybrids (with a seed yield higher than 105%) were obtained when at least one of the parental lines had a high TTC-reducing capacity. However, from these results it cannot be concluded which one is the best hybrid (e.g. in FIG. 6, line H3 had the best field score), and cannot be predicted which parental combinations would result in the highest heterosis.
The Best Performing Hybrid Lines can be Identified by Adding Acetylsalicylic Acid During the Incubation Period Heterosis is a phenomenon that is not well understood. Probably, various molecular, biochemical, and physiological factors contribute to the hybrid vigour phenotype (Griffing, 1990; Romangnoli et al., 1990; Titok et al., 1995; Tsaftaris, 1995; Zhang et al., 1996; Milborrow, 1998; Tsaftaris and Kafka, 1998; Xiong et al., 1998; Sun et al., 1999). Tolerance to stress could be one of these factors (Cassman, 1999). In fact, stress tolerance is the plant's ability to cope with suboptimal conditions, resulting in a relatively better growth and higher yield. If indeed hybrids are more tolerant to less favourable growth conditions, the tolerance of lines to stress could be used as an extra criterium to classify lines by vigour. To test this, the vigour assay was adapted by adding 0 and 25 mg/l acetylsalicylic acid to the incubation medium, imposing in this way oxidative stress on the explants (Chen et al., 1993; Dempsey and Klessig, 1994; Conrath et al., 1995; Xie and Chen, 1999). An example of the results obtained in these experiments is represented in FIG. 7A for four hybrid lines with different yield vigour (i.e. amount of seeds produced/ha compared to a standard control line). The line with the highest seed yield (line 41) showed the strongest decrease in TTC-reducing capacity after the acetylsalicylic acid treatment when compared to the control condition (no addition of acetylsalicylic acid). On the other hand the TTC-reducing capacity of the hybrid with the lowest seed yield (line 13) increased drastically after the acetylsalicylic acid treatment. This correlation between seed yield and the degree of decrease or increase of the TTC-reducing capacity after treatment with 25 mg/l acetylsalicylic acid versus the control condition (no addition of acetylsalicylic acid), was found for all the 28 hybrid lines that were tested (FIG. 7B).

Figure 7C:
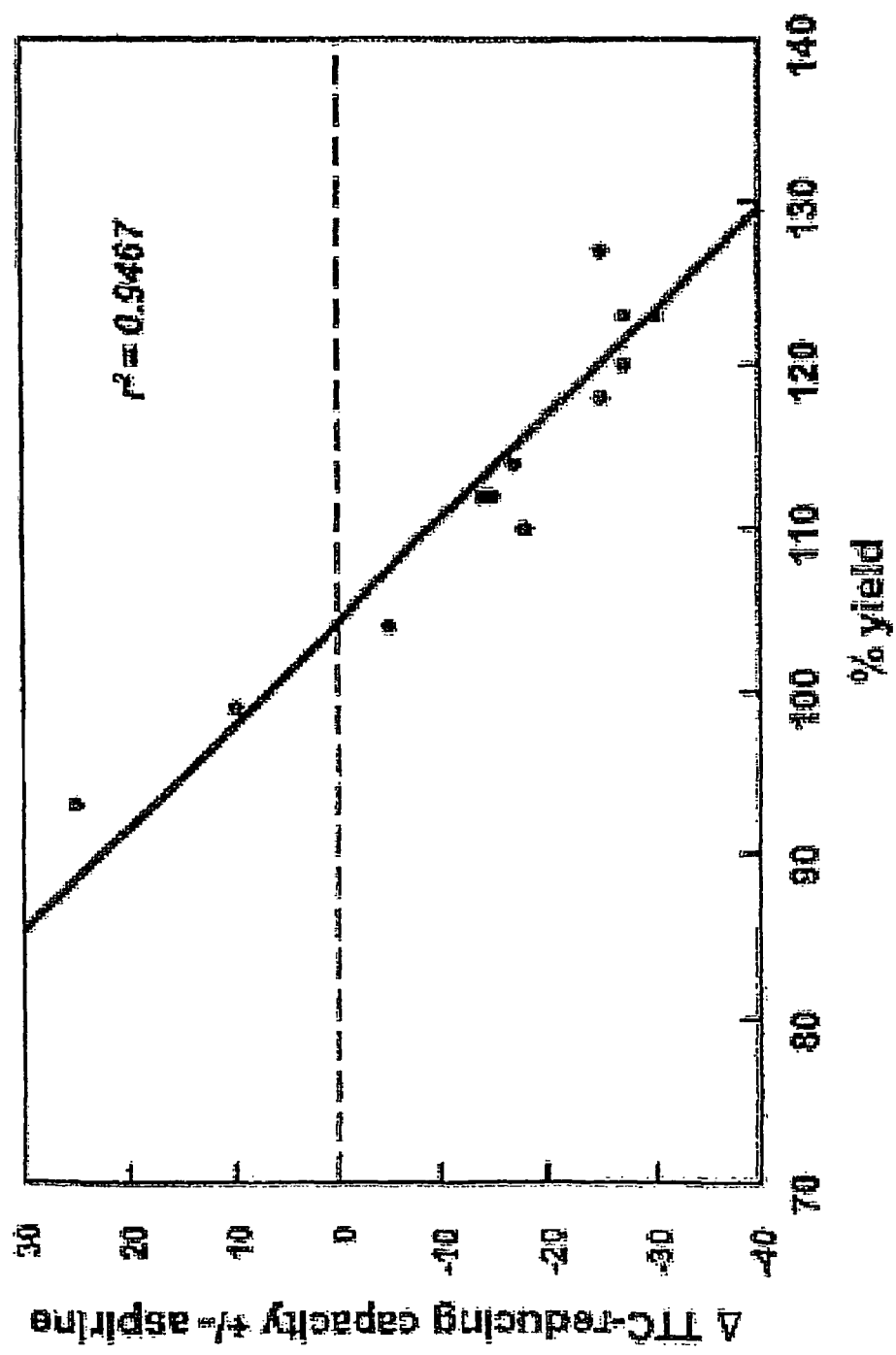
Figure 7D:
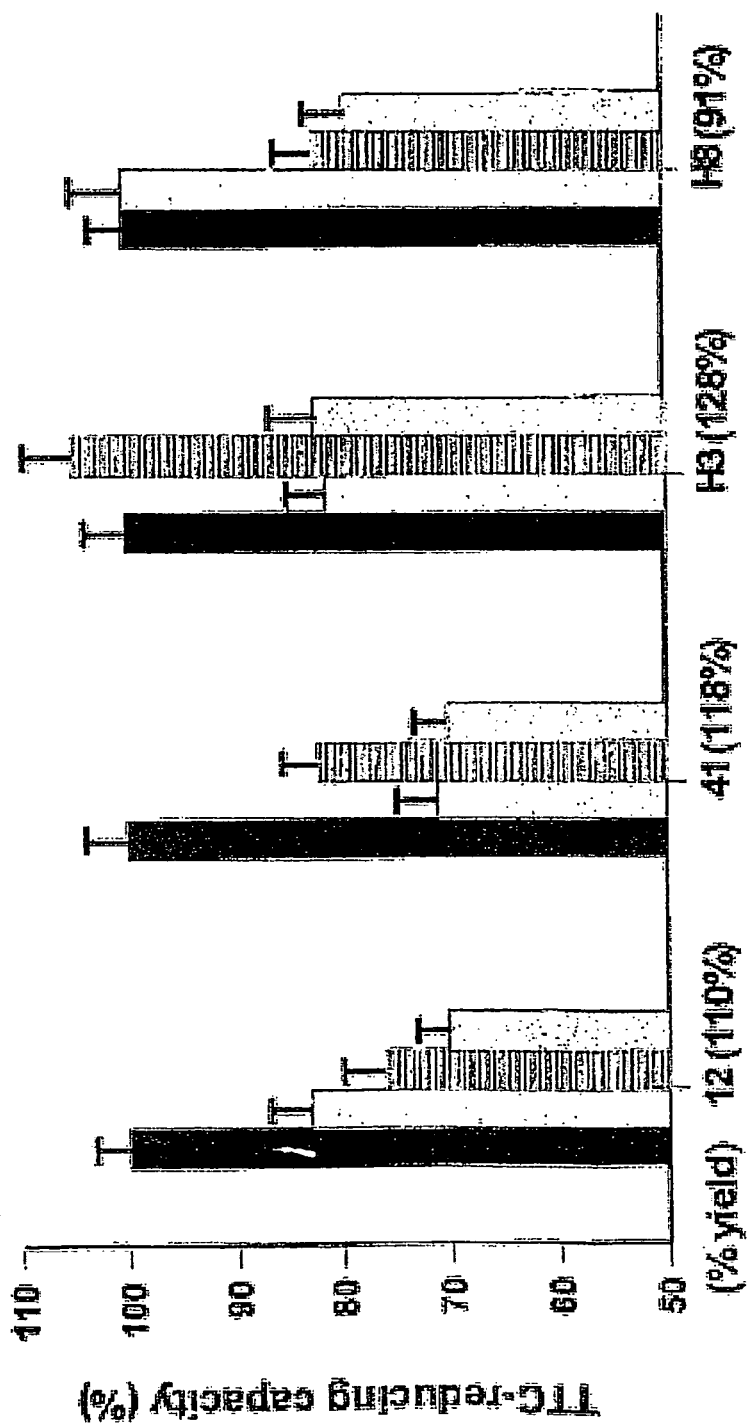

When the lines were subjected to higher concentrations of acetylsalicylic acid (50 and 100 mg/l) it was noticed that the TTC-reducing capacity of the best performing hybrid lines increased at 50 mg/l to decrease again at 100 mg/l acetylsalicylic acid. Hybrid lines with a less pronounced heterosis didn't show at 50 mg/l acetylsalicylic acid this increase in TTC-reducing capacity (FIG. 7C). The decrease in TTC-reducing capacity by acetylsalicylic acid in those hybrids with high seed yield, could be explained by an inhibition of both the cytochromal and alternative respiratory pathways (Xie and Chen, 1999).

In summary, the decrease in TTC-reducing capacity after treatment with 25 mg/l acetylsalicylic acid is more pronounced in hybrids with a high seed yield, while hybrid lines with a poor seed yield show at the same conditions from a minor decrease to a pronounced increase. The most heterotic hybrids, that have a significant decrease in TTC-reducing capacity at 25 mg/l acetylsalicylic acid, show at 50 mg/l acetylsalicylic acid an increase. This increase was never observed for the less performing hybrids.
The Increase by Acetylsalicylic Acid of the TTC-Reducing Capacity of the Less Vigorous Lines is not due to Reactive Oxygen Species but to an Increased Electron Flow Through the Cytochromal Pathway Although it is not described that TTC is reduced by reactive oxygen species, many tetrazolium dyes are reduced by superoxides (Raap, 1983; Seidler, 1991; Sutherland and Learmonth, 1997; Able et al., 1998). It is well known that salicylic acid generates reactive oxygen species (Chen et al., 1993; Dempsey and Klessig, 1994; Conrath et al., 1995; Rao and Davis, 1999; Xie and Chen, 1999) that could possibly reduce TTC. However, in these studies the formation of superoxides was quantified within hours after the application of salicylic acid. To test whether in our system the exogenous addition of acetylsalicylic acid still generates superoxides after 18 hours, the reduction of the tetrazolium salt XTT was measured. In the absence of the redox intermediate phenazine methosulphate (PMS), XTT is reduced only very slowly by cellular enzymes, but is reduced very efficiently by superoxides (Sutherland and Learmonth, 1997; Able et al., 1998). The results of these experiments revealed that after incubation for 18 hours in 25 mg/l acetylsalicylic acid, there is no significant difference in XTT-reducing capacity between the hypocotyl explants of the four hybrid lines with different vigour. In all the four lines lower amounts of XTT were reduced when the explants had been incubated for 18 hours in acetylsalicylic acid. These data indicate that after treatment for 18 hours with acetylsalicylic acid, the increase in TTC-reducing capacity by the weaker lines is not due to superoxides.

The stimulating effect of salicylic acid on the alternative respiratory pathway is well known (Rhoads and McIntosh, 1992; McIntosh, 1994; Van Der Straeten et al., 1995; Lambers, 1997), although Xie and Chen (1999) describe the inhibition by salicylic acid of both the cytochromal and the alternative oxidase pathways. In these papers the reaction of the plants to the salicylic acid applications was followed for only a few hours. In our experiments the explants were treated for a prolonged period (18 hours) with acetylsalicylic acid. In the previous experiment we showed that in the less vigorous lines superoxides are not responsible for the enhanced TTC-reduction by acetylsalicylic acid. For this we checked whether an enhanced cytochromal and/or alternative respiration could be the cause. The data obtained demonstrated that the enhanced TTC-reducing capacity after acetylsalicylic acid treatment is due to an increased electron flow through the cytochromal and not through the alternative respiratory pathway and this because the by acetylsalicylic acid enhanced TTC-reduction in the weaker line (line 13) is blocked by KCN and not by SHAM.

From these experiments it can be concluded that, in the described experimental conditions, a prolonged treatment with acetylsalicylic acid results: (1) in the vigorous lines in a reduction of the electron flow through the cytochromal pathway, (2) in the less vigorous lines in an enhancement of the electron flow through the cytochromal pathway.
The Vigour Assay can be used to Predict the Combining Ability of Parental Lines Although it is remarkable that the vigour assay allows to identify the best hybrids, it would be even more interesting for the breeder to identify the best parental combinations. The experiments described previously allow to predict which parental combinations will not result in heterotic hybrids: at least one of the parents needs to have a high TTC-reducing capacity at control conditions. To discriminate between the good and worse parental lines, the vigour assay was performed with and without acetylsalicylic acid treatment on parental lines with a known 'combining ability'. In FIG. 8, the relative TTC-reducing capacity under control conditions and after acetylsalicylic acid treatment, as well as the absolute TTC-reducing capacity under control conditions are represented. Similar to what was observed in the hybrids, the parental lines A and B with an excellent combining ability and that are used by the breeders as general combiners, have a decreased TTC-reducing capacity after acetylsalicylic acid treatment. The parental line DH7 with a poor combining ability, shows a high increase in TTC-reducing capacity after the acetylsalicylic acid treatment. The parental lines DH4, DH5 and DH10 with a moderate to good combining ability have no or only a small increase in TTC-reducing capacity after acetylsalicylic acid treatment. The reason that DH4 does not combine as well as DH10 with line A may be due to the lower total TTC-reducing capacity of line DH4.

These results together with the results shown in FIG. 6 imply that parental combinations will result in vigorous hybrids when: (1) at least one of the parental lines and preferentially both have a high TTC-reducing capacity, and (2) the TTC-reducing capacity of preferentially both parental lines is reduced by the acetylsalicylic acid treatment.

REFERENCES

Able, A J, Guest, D I., Sutherland, M W (1998) Plant Physiol 117: 491499
Cassman, K G (1999) Proc. Natl. Acad. Sci. USA 96: 5952-5959
Chen, H-H, Shen, Z-Y, Li, P H (1982) Crop Science 22: 719-725
Chen, Z, Silva, H, Kiessig, D F (1993 Science 262: 1883-1886
Conrath, U, Chen, Z, Ricigliano, J R, Klessig, D F (1995) Proc Natl Acad Sci USA 92: 7143-7147
Dempsey, D A, Klessig, D F (1994) Trends Cell Biol 4: 334-338
Duncan, D R, Widholm, J M (1990) In J W Pollard, J M Walker, eds, Methods in Molecular Biology, Vol 6. Plant Cell and Tissue Culture. Humana Press, Clifton, N.J., pp 29-37
Enikeev, A G, Vysotskaya, E F, Lionova, L A, Gamburg, K Z (1995) Russ J Plant Physiol 42(3): 372-375
Goodwin, C J, Holt, S J, Downes, S, Marshall, N J (1995) Journal of Immunological Methods 179: 95-103
Graham, G I, Wolff, D W, Stuber, C W (1997) Crop Sci 37: 1601-1610
Griffing, B (1990) Genetics 126: 753-767
Hyslop, P A, Hinshaw, D B, Halsey Jr, W A, Schraufstätter, I U, Sauerheber, R D, Spragg,
R G, Jackson, J H, Cochrane, C G (1988) J Biochem Chem 263(4): 1665-1675
Jovilet, Y, Pireaux, J-C, Dizengremel, P (1990) Plant Physiol 94: 641-646
Kim, C S, Jung, J (1995) J Photochem Photobiol 29: 135-139
Lin, T-Y, Markhart III, A H (1990) Plant Physiol 94: 54-58
Kumar, S, Kumar Acharya, S (1999) Anal Biochem 268: 89-93
Lambers, H (1997) Respiration and the alternative oxidase. In C H Foyer, W P Quick, eds, A molecular approach to primary metabolism in higher plants. Taylor & Francis Ltd, UK, pp 295-309
Larsen, S U, Povisen, F V, Eriksen, E N, Pedersen, H C (1998) Seed Sci and Technol 26: 627-641
Lichtenthaler, H K (1996) J Plant Physiol 148: 4-14
Lichtenthaler, H K, Miehé, J A (1997) Trends Plant Sci 2(8): 316-320
Mcintosh, L (1994) Plant Physiol 105: 781-786
Milborrow, B V (1998) J Exp Bot 49(324): 1063-1071
Millar, A H, Atkin, O K, Lambers, H, Wiskich, J T, Day, D A (1995) Physiol Plant 95: 523-532
Minagawa, N, Koga, S, Nakano, M, Sakajo, S, Yoshimoto, A (1992) FEBS Letters 302(3): 217-219
Moller, I M, Bérczi, A, van der Plas, L H W, Lambers, H (1988) Physiol Plant 72: 642-649
Moore, A L, Siedow, J N (1991) Biochem Biophys Act 1059: 121-140
Murashige, T, Skoog, F (1962) Physiol Plant 15: 473-497
Musser, D A, Oseroff, A R (1994) Phytochem Photobiol 59(6): 621-626
Popov, A S, Vysotskaya, O N (1996) Russian J Plant Physiol 43(2): 263-269
Raap, A K (1983) Histochem J 15: 977-986
Rao, M V, Davis, K R (1999) Plant J 17(6): 603-614
Rawyler, A, Pavelic, D, Giainazzi, C, Oberson, J, Braendle, R (1999) Plant Physiol 120: 293-300
Rhoads, D M, Mcintosh, L (1992) Plant Cell 4: 1131-1139
Ribas-Carbo, M, Aroca, R, Gonzàles-Meler, M A, Irigoyen, J J, Sánchez-Dias, M (2000) Plant Physiol 122: 199-204
Rich, P. R., Mischis, L. A., Purton, S., Wiskich, J. T. (2001) FEMS Microbiol. Letters 202: 181-187
Romangnoli, S, Maddaloni, M, Livini, C, Motto, M (1990) Theor Appl Genet 80: 769-775
Seidler, E (1991) Progress in Histochemistry and Cytochemistry 24: 1-86
Stepan-Sarkissian, G, Grey, D (1990) Growth determination and medium analysis. In J W Pollard, J M Walker, eds, Methods in Molecular Biology, Vol 6. Plant Cell and Tissue Culture. Humana Press, Clifton, N.J., pp 13-27
Strydom, A, Van de Venter, H A (1998) Seed Sci and Technol 26: 579-585
Sun, Q, Ni, Z, Liu, Z (1999) Euphytica 106: 117-123
Sutherland, M W, Learmonth, B A (1997) Free Rad Res 27(3): 283-289
Titok, W, Rusinova, O V, Khotyleva, L V (1995) Biol Plant 37(4): 507-513
Towill, L E, Mazur, P (1975) Can J Bot 53: 1097-1102
Tsaftaris, A S, Kafka, M (1998). J Crop Production 1(1): 95-111
Tsaftaris, S A (1995) Physiol Plant 94: 362-370
Upadhyaya, A, Caldwell, C R (1993) Environ Exp Bot 33(3): 357-365
Van Der Straeten, D, Chaerle, L, Sharkov, G, Lambers, H, Van Montagu, M (1995) Planta 196: 412-419
Vanlerberghe, G C, Mcintosh, L (1996) Plant Physiol 111: 589-595
Wagner, A M, Krab, K (1995) Physiol Plant 95: 318-325
Xiao, J, Li, J, Yuan, L, Tanksley, S D (1995) Genetics 140: 745-754
Xie, Z, Chen, Z (1999) Plant Physiol 120: 217-225
Xiong, L Z, Yang, G P, Xu, C G, Zhang, Q, Saghai Maroof, M A (1998) Mol Breeding 4: 129-136
Zhang, Q, Zhou, Z Q, Yang, G P, Xu, C G, Liu, K D, Saghai Maroof, M A (1996) Theor Appl Genet 93: 1218-1224

I claim:

1. A method for producing a hybrid *Brassica* plant line, comprising the steps of:
   a) assaying a collection of *Brassica* inbred plant lines of interest by
      i) culturing a population of explants of each of said *Brassica* inbred plant lines of said collection on a medium comprising sucrose or on callus inducing medium comprising sucrose and plant hormones for a period of 0 to 10 days;
      ii) measuring the electron flow in the mitochondrial electron transport chain in said population of explants, relative to the electron flow in the mitochondrial electron transport chain in a population of explants from a reference plant line of the same species;

b) assaying said collection of inbred lines of interest by
  i) culturing a population of explants of each of said inbred *Brassica* plant lines of said collection on a medium comprising sucrose or on callus inducing medium comprising sucrose and plant hormones;
  ii) incubating a first part of each of the populations of said cultured explants in a buffer solution;
  iii) incubating a second part of each of the populations of said cultured explants in said buffer solution, further comprising a salicylic acid derivative capable of generating oxidative stress in plant cells incubated in a solution of said salicylic acid derivative;
  iv) measuring the electron flow in the mitochondrial electron transport chain in each of said first and second parts of said populations;
c) selecting one inbred plant line which has a higher relative amount of electron flow in the mitochondrial electron transport chain when compared to other inbred lines from said collection as determined in step (a) and which has a negative difference between the measured electron flow in the mitochondrial electron transport chain between said second and said first part as measured in step (b);
d) crossing said selected inbred plant line with a second inbred plant line;
e) collecting seed from said crossed selected inbred plant line.

2. The method of claim 1, wherein said second inbred line has a higher relative amount of electron flow in the mitochondrial electron transport chain when compared to other inbred lines from said collection and has a negative difference between the measured electron flow in the mitochondrial electron transport chain between said second and said first part.

3. The method any one of claim 1 or 2, wherein said parts of said population of cultured explants are incubated in said buffer solution for about 18 hours.

4. The method of claim 1, wherein said buffer solution comprises about 25 mM K-phosphate and about 2 to 3% sucrose.

5. The method of claim 1, wherein said salicylic acid derivative is acetylsalicylic acid.

6. The method of claim 5, wherein said acetylsalicylic acid is present in said buffer solution in a concentration of about 25 mg/L.

7. The method of claim 1, wherein said explant is a hypocotyl.

8. The method of claim 1, wherein said reference plant line of the same species is a reference plant line of the same variety.

9. The method of claim 1, wherein said period is 4 to 6 days.

10. The method of claim 1, wherein said period is 5 days.

* * * * *